(12) United States Patent
Munoz et al.

(10) Patent No.: US 7,495,029 B2
(45) Date of Patent: Feb. 24, 2009

(54) PRODRUGS OF (2R)-2-PROPYLOCTANOIC ACID FOR THE TREATMENT OF STROKE

(75) Inventors: Benito Munoz, San Diego, CA (US); Joseph E. Payne, Oceanside, CA (US); Petpiboon Prasit, Rancho Santa Fe, NJ (US); Thomas S. Reger, Lansdale, PA (US); Nicholas D. Smith, San Diego, CA (US)

(73) Assignee: Merck & Co., Inc, Rahway, NJ (US)

( * ) Notice: Subject to any disclaimer, the term of this patent is extended or adjusted under 35 U.S.C. 154(b) by 0 days.

(21) Appl. No.: 11/667,814

(22) PCT Filed: Nov. 10, 2005

(86) PCT No.: PCT/US2005/040727

§ 371 (c)(1),
(2), (4) Date: May 15, 2007

(87) PCT Pub. No.: WO2006/055381

PCT Pub. Date: May 26, 2006

(65) Prior Publication Data

US 2008/0132488 A1     Jun. 5, 2008

Related U.S. Application Data

(60) Provisional application No. 60/628,280, filed on Nov. 16, 2004.

(51) Int. Cl.
*A61K 31/235* (2006.01)
*C07J 71/00* (2006.01)
*C07D 311/80* (2006.01)
*C07C 381/00* (2006.01)
*C07C 69/02* (2006.01)

(52) U.S. Cl. .......... 514/532; 540/75; 549/390; 560/9; 560/231

(58) Field of Classification Search ............ None
See application file for complete search history.

(56) References Cited

U.S. PATENT DOCUMENTS

| | | | |
|---|---|---|---|
| 4,791,207 A * | 12/1988 | Salzmann et al. | 548/110 |
| 5,641,792 A * | 6/1997 | Kleemann et al. | 514/351 |
| 5,733,909 A | 3/1998 | Black et al. | |
| 5,849,943 A | 12/1998 | Atkinson et al. | |
| 5,925,631 A | 7/1999 | Black et al. | |
| 6,020,343 A | 2/2000 | Belley et al. | |
| 6,057,319 A | 5/2000 | Black et al. | |
| 6,201,021 B1 * | 3/2001 | Ohuchida et al. | 514/558 |
| 6,608,221 B1 | 8/2003 | Toda et al. | |

FOREIGN PATENT DOCUMENTS

JP    2006016318 A    1/2006

* cited by examiner

*Primary Examiner*—Paul A Zucker
(74) *Attorney, Agent, or Firm*—William Krovatin; John C. Todaro

(57) ABSTRACT

Disclosed are prodrugs of (2R)-2-propyloctanoic acid, and pharmaceutical compositions comprising them, which may be effective in modulating multiple events in the biochemical cascade of stroke. Also disclosed are methods of treating patients who have had a stroke, or are at risk of stroke, by administering the compounds or compositions of the invention.

15 Claims, No Drawings

PRODRUGS OF (2R)-2-PROPYLOCTANOIC ACID FOR THE TREATMENT OF STROKE

CROSS-REFERENCE TO RELATED APPLICATIONS

This application claims priority under 35 U.S.C. §119(e) to U.S. provisional application Ser. No. 60/628,280, filed Nov. 16, 2004.

FIELD OF THE INVENTION

This invention is directed to prodrugs of (2R)-2-propyloctanoic acid which are useful for treating stroke, and pharmaceutical compositions comprising the compounds of the invention. The invention is also directed to methods of treating patients who have had a stroke or are at risk of stroke, by administering to the patient a compound or pharmaceutical composition of the invention.

BACKGROUND OF THE INVENTION

Stroke is a cerebrovascular event, which occurs when the normal bloodflow to the brain is disrupted, and the brain receives too much or too little blood. Stroke is one of the leading causes of death worldwide, and is also one of the most common causes of neurologic disability.

Ischemic stroke, which is the most common type of stroke, results from insufficient cerebral circulation of blood caused by obstruction of the inflow of arterial blood. Normally, adequate cerebral blood supply is ensured by a system of arteries within the brain. However, various disorders, including inflammation and atherosclerosis, can cause a thrombus, i.e., a blood clot that forms in a blood vessel. The thrombus may interrupt arterial blood flow, causing brain ischemia and consequent neurologic symptoms. Ischemic stroke may also be caused by the lodging of an embolus (an air bubble) from the heart in an intracranial vessel, causing decreased perfusion pressure or increased blood viscosity with inadequate cerebral blood flow. An embolus may be caused by various disorders, including atrial fibrillation and atherosclerosis.

A second type of stroke, hemorrhagic stroke, involves a hemorrhage or rupture of an artery leading to the brain. Hemorrhagic stroke results in bleeding into brain tissue, including the epidural, subdural, or subarachnoid space of the brain. A hemorrhagic stroke typically results from the rupture of an arteriosclerotic vessel that has been exposed to arterial hypertension or to thrombosis.

During acute ischemic stroke, i.e., the period from the cerebrovascular event up to 24 hours after the event, the arterial occlusion results in an immediate infarcted core of brain tissue, where cerebral blood flow is significantly reduced, for example to less than 20% of the normal blood flow. The infarcted core suffers irreversible damage due to significant cell death. The length of time that ischemia persists, and the severity of the ischemia, contribute to the extent of injury. An area around the infracted core, known as the ischemic penumbra, suffers a delayed and less severe infarct. For example, during acute stroke the penumbra may have a reduction in blood flow of from about 20-40% of normal blood flow.

While not fully understood, the pathogenesis of ischemic stroke involves a complex cascade of multiple interacting biochemical events, which lead to acute neurologic injury and reduced neurological function. Ischemia results in the depletion of cellular energy stores of ATP, and the failure of sodium and potassium ion pumps. This leads to depolarization of neurons in the brain, and consequent excitotoxicity, i.e. excessive activity of excitatory amino acids, including glutamate, resulting in neuronal damage. In addition, the cascade leads to an increase in intracellular calcium. The presence of intracellular calcium in turn leads to the activation of intracellular enzymes and neuronal death. Lyden et al., *J Stroke and Cerebrovasc Dis* 2000;9 (6, Suppl 2);9-14. Excitotoxicity also results in the activation of enzymes, phospholipases, proteases, and nitric oxide synthases, and the production of oxygen free radicals. Each of these events contribute to the neuronal cell death of stroke. Nicotera et al, *J Cerebr Blood Flow & Metab* 19(6); 583-591 (1999).

One opportunity for pharmacologic intervention in stroke is the prevention or reduction of risk of stroke in patients at risk for stroke. There are many known risk factors for stroke, including vascular inflammation, atherosclerosis, arterial hypertension, diabetes, hyperlipidemia and atrial fibrillation. At risk patients have been treated with agents to control blood pressure or manage blood lipid level, and have been treated with antiplatelet agents (such as clopidrogel) and anticoagulants. Patients who have suffered myocardial infarction and are at risk for stroke are often treated with angiotensin-converting enzyme inhibitors (ACE inhibitors) or beta adrenergic antagonists (beta blockers).

A second opportunity for pharmacological treatment of stroke is the treatment of acute stroke. However, current pharmacologic therapies for treating acute stroke are limited to restoring blood flow within a narrow therapeutic time window of less than three hours after stroke. The only agents which have shown effectiveness in treating acute stroke are thrombolytics (such as rt-PA) and urokinase. There remains a need for agents which are effective within a longer therapeutic time window.

Another opportunity for pharmacological treatment of stroke is recovery or restoration after the acute stroke period, i.e. the reduction or prevention of secondary cell damage in the penumbra. Although some neuroprotective agents have demonstrated efficacy in preclinical animal models of stroke, favorable results have not always been duplicated in human clinical trials. There remains a need for agents which are effective in reducing or preventing secondary cell damage after stroke.

It would be desirable to obtain a single pharmaceutical agent which can be used in more than one of the above-mentioned opportunities for treating stroke. Such an agent may be administered to patients at risk for stroke, and also may be administered to patients suffering from acute stroke, or patients undergoing treatment for recovery or restoration after the acute stroke period. Such an agent may also target more than one distinct mechanism in the biochemical cascade of stroke.

One class of neuroprotective agents which are known to be useful for treating stroke are reactive astrocyte inhibitors. Astrocytes are a type of cell found in the central nervous system. Astrocytes supply essential substrates and remove toxins from the area of the brain surrounding neurons, and help to maintain suitable levels of antioxidants in the brain. See Wilson et al, *Can J Physiol Pharmacol* 75:1149-1163 (1997). However, recent evidence indicates that astrocytes may have a broader role in the modulation of neural networks. For example, astrocytes may express voltage gated ion channels and neurotransmitter receptors. Bachoo et al, *Proc Nat'l Acad Sci*, 101:8384-8389 (2004).

Thus, compounds which may inhibit the production of reactive astrocytes may be useful in the treatment of stroke. A preferred inhibitor of reactive astrocytes is (2R)-2-propyloctanoic acid, shown below:

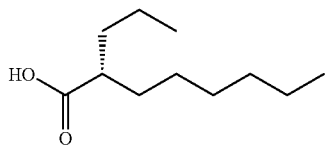

which is disclosed in U.S. Pat. No. 6,608,221.

SUMMARY OF THE INVENTION

In one embodiment, the invention is directed to compounds that are useful for prodrugs for the treatment of stroke, comprising (2R)-2-propyloctanoic acid which is linked to another agent which is involved in the treatment of stroke. Upon dosing, the compounds of the invention will be modified in vivo to form (2R)-2-propyloctanoic acid, and the other agent which targets additional mechanisms involved in the biochemical cascade resulting in the progression of stroke.

For example, in one embodiment the invention is directed to compounds of formula (I)

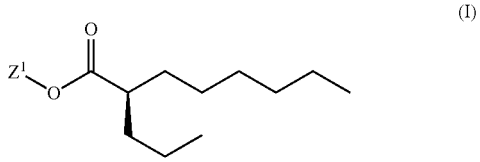

or pharmaceutically acceptable salts thereof, wherein $Z^1$ is a pharmaceutically active compound that modulates one or more of the biochemical events occurring during stroke. The $Z^1$ moiety is modified in vivo to form the compound which modulates the biochemical event.

$Z^1$ may be, for example, a COX-2 inhibitor, a nitric oxide synthase inhibitor, a Rho kinase inhibitor, an angiotension II type-1 receptor antagonist, a glycogen synthase kinase 3 inhibitor, a sodium or calcium channel blocker, a p38 MAP kinase inhibitor, a thromboxane AX-synthetase inhibitor, a statin (an HMG CoA reductase inhibitor), a neuroprotectant, a beta andrenergic blocker, a NMDA receptor antagonist, a platelet fibrinogen receptor antagonist, a thrombin inhibitor, an antihypertensive agent or a vasodilator. $Z^1$ may also be a compound which is known to be neuropharmacologically active or is known or believed to be effective in treating stroke, such as lithium ion, valproic acid, sodium 4-phenyl butyrate or uridine.

In another embodiment, the invention is directed to compounds of formula (II)

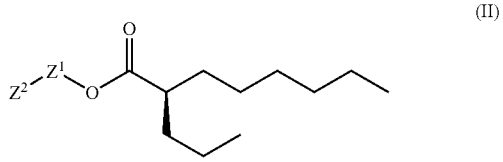

or pharmaceutically acceptable salts thereof, wherein each of $Z^1$ and $Z^2$ is a pharmaceutically active compound that modulates one or more of the biochemical events occurring during stroke, as defined above. The $Z^1$ and $Z^2$ moieties are modified in vivo to form the compound which modulates the biochemical event.

In another embodiment of the compounds of formula (II), $Z^1$ is a pharmaceutically active compound that modulates one or more of the biochemical events occurring during stroke as defined above and $Z^2$ is a moiety that imparts a favorable property, for example solubility in an aqueous media, to the compound of formula (II).

DETAILED DESCRIPTION OF THE INVENTION

The compounds of the present invention have utility in treating, ameliorating or controlling stroke and the neurologic injuries caused by stroke.

As used herein, the term "stroke" refers to a clinical event involving impairment of cerebral circulation, that results in neurologic injury. Typically, stroke is manifest by the abrupt onset of a focal neurologic deficit. Stroke results from a rupture or obstruction (as by a thrombus or embolus) of an artery of the brain.

As used herein, the term "ischemic stroke" refers to stroke characterized by localized tissue anemia due to obstruction of the inflow of arterial blood. Ischemic stroke is usually caused by atherothrombosis or embolism of a major cerebral artery, but may also be caused by coagulation disorders or non-atheromatous vascular disease.

The subject or patient to whom a compound of the present invention is administered is generally a human being, male or female, in whom treatment of stroke is desired, but may also encompass other mammals, such as dogs, cats, mice, rats, cattle, horses, sheep, rabbits, monkeys, chimpanzees or other apes or primates, for which treatment of stroke is desired.

One class of patients to which a compound of the invention may be administered is a patient at risk for stroke. As used herein, the term "patient at risk for stroke" means an individual who has had a previous stroke, or has a risk factor for stroke. Known risk factors for stroke include atherosclerosis, arterial hypertension, lipohyalinosis, hyperlipidemia, hypercholesterolemia, atrial fibrillation, smoking, inflammatory markers (including C-reactive protein), infection, homocysteine, sleep-disordered breathing, cerebral autosomal dominant arteriopathy with subcortial infarcts and leuko-encephalopathy (CADASIL), migraine, sickle-cell anemia, antiphospholipid antibody syndrome, arterial dissection, cocaine abuse and obesity.

As used herein, the term "treatment" or "treating" means any administration of a compound of the present invention and includes (1) inhibiting stroke or the symptoms of stroke in an animal that is experiencing or displaying the pathology or symptomatology of stroke (i.e., arresting further development of the pathology and/or symptomatology), or (2) ameliorating stroke or the symptoms of stroke in an animal that is experiencing or displaying the pathology or symptomatology of stroke (i.e., reversing the pathology and/or symptomatology). The term "controlling" includes preventing, treating, eradicating, ameliorating or otherwise reducing the severity of stroke, or reducing the risk of stroke.

Efforts at "controlling" stroke (including preventing stroke) can be divided into the primary prevention of stroke (treatment of patients who have not had any prior transient ischemic attacks of strokes, and have no neurological symptoms) and secondary prevention of stroke (treatment of patients who have had a prior transient ischemic attack or stroke). Primary prevention of stroke includes non-pharmacologic interventions, such as smoking cessation, healthy eating patterns, increased physical activity and weight management. Primary prevention also includes certain pharmacologic interventions, such as blood pressure control, treatment of atrial fibrillation, and management of diabetes, if appropriate. As part of the primary prevention of stroke, patients at high risk of coronary heart disease are often treated with aspirin. As part of primary prevention, patients having high amounts of low density lipoprotein (LDL) are often subject to blood lipid management, to reduce LDL levels to acceptable levels, e.g. below 160 mg/dl.

The secondary prevention of stroke often involves the same pharmacologic and non-pharmacologic interventions used for primary prevention, including blood pressure control, treatment of atrial fibrillation, management of diabetes, treatment with aspirin, and blood lipid management. Additional common secondary prevention interventions include the use of antiplatelet agents (such as clopidrogel), anticoagulants (such as warfarin), and anti-hypertension agents (such as beta andrenergic antagonists).

A second class of patients to which a compound of the invention may be administered are acute stroke patients, i.e., patients who have suffered ischemic stroke within the last 7 days. One preferred class of acute stroke patients are those who have suffered stroke within the last 3 days. A more preferred class of acute stroke patients are those who have suffered stroke within the last 48 hours, even more preferably within the last 24 hours. As common in the art of treating stroke, patients may be classified according to the period of time when stroke occurred. So, for example, one class of acute stroke patients are those who have suffered stroke within the last 18 hours. Another class of acute stroke patients are those who have suffered stroke within the last 12 hours. Another class of acute stroke patients are those who have suffered stroke within the last 8 hours. Another class of acute stroke patients are those who have suffered stroke within the last 6 hours. Another class of acute stroke patients are those who have suffered stroke within the last 4 hours. Another class of acute stroke patients are those who have suffered stroke within the last 3 hours.

Treatment of acute stroke, i.e. treatment during the cerebral event causing stroke and the 7 days thereafter, involve treatment with thrombolytics such as recombinant tissue plasminogen activator (rtPA). However, rtPA has only been approved for treatment of acute stroke for use within the first three hours after stroke. Another potential agent for treatment of acute stroke is the neuroprotectant edaravone, which has been approved in Japan.

During acute ischemic stroke, the arterial occlusion caused by the thrombus or embolus results in an immediate infarcted core of brain tissue, where cerebral blood flow is significantly reduced, for example to less than 20% of the normal blood flow. The infarcted core suffers irreversible damage due to significant cell death. The length of time that ischemia persists, and the severity of the ischemia, contribute to the extent of the infarct. An area around the infracted core, known as the ischemic penumbra, suffers a delayed and less severe infarct. For example, during acute stroke the penumbra may have a reduction in blood flow of from about 20-40%.

Patients who have suffered stroke more than 24 hours previously often develop cerebral edema which typically occurs at from one to five days after stroke. As used herein, the term "cerebral edema" refers to fluid collecting in brain tissue due to cellular swelling and the breakdown of the blood-brain barrier. Post-stroke cerebral edema may also involve the exuding of cerebrospinal fluid from ependymal lining, or the creation of an osmotic environment due to blood clots or tissue injury. The osmotic environment allows the movement of water into interstitial spaces. Post-stroke cerebral edema is often responsible for a worsening in the stroke patient's clinical status.

A third class of patients to which a compound of the present invention may be administered are patients who have suffered stroke more than 7 days previously, who are typically in need of restorative treatment.

The terms "administration of" or "administering a" compound should be understood to mean providing a compound of the invention to the individual in need of treatment in a form that can be introduced into that individual's body in a therapeutically useful form and therapeutically useful amount.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of stroke, particularly in a patient who demonstrates symptoms of stroke.

As used herein, the term "prodrug" refers to a molecule that is inert, i.e. not pharmacologically active, but that has pharmacological activity upon activation by a biological system. For example, a prodrug is a compound which is inert when in a tablet, capsule or other pharmaceutical composition, but is modified and becomes pharmacologically active in vivo, upon ingestion by a mammal. Thus, compounds of formula (I) and (II), which are modified in vivo to release compounds which are pharmacologically active in the treatment of stroke, are prodrugs.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid and the like. Particularly preferred are citric, hydrobromic, hydrochloric, maleic, phosphoric, sulfuric, fumaric, trifluoroacetic and tartaric acids.

Suitable $Z^1$ and $Z^2$ groups include a COX-2 inhibitor, a nitric oxide synthase inhibitor, a Rho kinase inhibitor, an angiotension II type-1 receptor antagonist, a glycogen synthase kinase 3 inhibitor, a sodium or calcium channel blocker, a p38 MAP kinase inhibitor, a thromboxane AX-synthetase inhibitor, a statin (an HMG CoA reductase inhibitor), a neuroprotectant (including an antioxidant, an NMDA receptor antagonist, an NR2B antagonist, a sodium or calcium channel blocker, and a 5-HT1A agonist), a beta andrenergic blocker, a NMDA receptor antagonist, a platelet fibrinogen receptor antagonist, a thrombin inhibitor, an antihypertensive agent or a vasodilator. Suitable $Z^1$ or $Z^2$ groups also include compounds which are known to be neuropharmacologically active or are known or believed to be effective in treating stroke, such as lithium ion, valproic acid, sodium 4-phenyl butyrate or uridine.

Each class of compounds is discussed further below.

COX-2 Inhibitors

One class of compounds which may be useful as $Z^1$ and $Z^2$ moieties are cycloxygenase-2 inhibitors. Selective inhibitors of COX-2 have similar antiinflammatory, antipyretic and analgesic properties to conventional non-steroidal antiinflammatory drug, but have a diminished ability to induce some of the mechanism-based side effects. In particular, selective COX-2 inhibitors have a reduced potential for gastrointestinal toxicity, a reduced potential for renal side effects, a reduced effect on bleeding times and possibly a lessened ability to induce asthma attacks in aspirin-sensitive asthmatic subjects.

COX-2 inhibitors have been demonstrated in animal studies to improve ischemia-induced behavioral deficits, and thus selective COX-2 inhibitors may be useful in the treatment of ischemic stroke to improve behavioral functions. See Lapchak et al, *Stroke* 32:1220 (2001).

Exemplary COX-2 inhibitors enclosed rofecoxib (marketed as VIOXX™), celecoxib (marketed as CELEBREX™), meloxicam (marketed as MOBICOX™).

In one embodiment, the $Z^1$ or $Z^2$ moiety is one of a class of furan-2-one derivative COX-2 inhibitors, and prodrugs thereof, which have been disclosed in U.S. Pat. Nos. 5,733,909, 5,849,943, 5,925,631, 6,020,343 and 6,057,319. Furan-2-one COX-2 inhibitors have demonstrated a reduction in infarct volume in the middle cerebral artery occlusion (MCAO) stroke model. For example, DFU (5,5-dimethyl-3-(3-fluorophenyl)-4-(4-methylsulphonyl-2(5H)-furanone), which is disclosed in U.S. Pat. No. 6,020,343, has been shown to be neuroprotective against hippocampal damage in gerbils subjected to a transient global ischemia event (Jalil, et al, *Brain Research*, 927, 2002, 212-215), and has also been shown to dose dependently reduce endotoxin-induced mortality in mice (Tunctan et al, *Pharmacological Res* 2003, 48, 37-48).

In this embodiment, the $Z^1$ or $Z^2$ moiety is depicted in Formula (III) below:

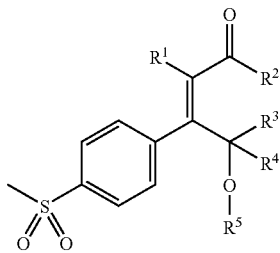

wherein:
$R^1$ is selected from the group consisting of
(1) -Q-$R^a$,
(2) a carbocyclic group having from 3 to 8 ring atoms, optionally having from one to three ring heteroatoms selected from the group consisting of S, N and O,
(3) —$C_{6-10}$ aryl, and
(4) heteroaryl,
wherein said carbocyclic group, aryl and heteroaryl are unsubstituted or substituted with one or more
(a) halogen,
(b) cyano,
(c) $NO_2$,
(d) —$C_{1-6}$ alkyl, wherein said alkyl is unsubstituted or substituted with one or more halogen,
(e) —$C_{1-6}$ alkoxy,
(f) —C(=O)—(O)—$R^b$
(g) —C(=O)—$NR^bR^{b'}$
(h) —O—C(=O)—$R^b$
(i) —S—$C_{1-6}$ alkyl,
(j) —S(O)$_x R^b$,
(k) —S(O)$_x NR^b R^{b'}$,
(l) —S(O)$_x NR^b C(=O)C_{1-6}$ alkyl, wherein said alkyl is unsubstituted or substituted with one or more halogen,
(m) —$NR^b R^{b'}$,
(n) —$NR^b$—C(=O)—$R^{b'}$,
(o) —P(=O)$R^b$OH,
(p) —P(=O)$R^b NH_2$, and
Q is selected from the group consisting of
(a) —O—,
(b) —S—,
(c) —$SO_2$—,
(d) —$NR^b$,
$R^a$, $R^b$ and $R^{b'}$ are independently selected from the group consisting of:
(a) hydrogen,
(b) —$C_{1-10}$ alkyl,
(c) —$C_{2-10}$ alkenyl,
(d) —$C_{2-10}$ alkynyl,
(e) a carbocyclic group having from 3 to 8 ring atoms, optionally having from one to three ring heteroatoms selected from the group consisting of S, N and O,
(f) —$C_{6-10}$ aryl, and
(g) heteroaryl,
wherein said carbocyclic group, alkyl, alkenyl, alkynyl, aryl and heteroaryl are unsubstituted or substituted with one or more
(i) halogen,
(ii) cyano,
(iii) —$NO_2$,
(iv) —$C_{1-6}$ alkyl, wherein said alkyl is unsubstituted or substituted with one or more halogen,
(v) —$C_{1-6}$ alkoxy,
(vi) —C(=O)—(O)—$R^c$
(vii) —C(=O)—$NR^c R^{c'}$
(viii) —O—C(=O)—$R^c$
(ix) —S—$C_{1-6}$ alkyl,
(x) —S(O)$_x R^c$,
(xi) —S(O)$_x NR^c R^{c'}$,
(xii) —S(O)$_x NR^c C(=O)C_{1-6}$ alkyl, wherein said alkyl is unsubstituted or substituted with one or more halogen,
(xiii) —N $R^c R^{c'}$,
(xiv) —$NR^c$—C(=O)—$R^{c'}$,
(xv) —P(=O)$R^c$OH,
(xvi) —P(=O)$R^c NH_2$,
and $R^c$ and $R^{c'}$ are independently selected from the group consisting of
(A) hydrogen,
(B) —$C_{1-10}$ alkyl,
(C) —$C_{2-10}$ alkenyl,
(D) —$C_{2-10}$ alkynyl, (E) a carbocyclic group having from 3 to 8 ring atoms, optionally having from one to three ring heteroatoms selected from the group consisting of S, N and O,
(F) —$C_{0-10}$ alkyl-$C_{6-10}$ aryl, and
(G) heteroaryl;

$R^2$ is selected from the group consisting of
(1) —$OR^d$,
(2) —$NR^d R^{d'}$,
and $R^d$ and $R^{d'}$ are selected from the same group as $R^c$ and $R^{c'}$;

$R^3$ and $R^4$ are independently selected from the group consisting of
(1) hydrogen,
(2) —$C_{1-10}$ alkyl,
(3) —$C_{2-10}$ alkenyl,
(4) —$C_{2-10}$ alkynyl,
(5) —$C_{6-10}$ aryl, or
(6) heteroaryl,
wherein said alkyl, alkenyl, alkynyl, aryl and heteroaryl are unsubstituted or substituted with one or more
(a) halogen,
(b) cyano,
(c) $NO_2$,
(d) $C_{1-6}$ alkyl, wherein said alkyl is unsubstituted or substituted with one or more halogen,
(e) —$C_{1-6}$ alkoxy,
(f) —C(=O)—(O)— $R^e$
(g) —C(=O)—$NR^e R^{e'}$
(h) —O—C(=O)— $R^e$
(i) —S—$C_{1-6}$ alky,
(j) —$S(O)_x R^e$,
(k) —$S(O)_x NR^e R^{e'}$,
(l) —$S(O)_x NR^e C(=O)C_{1-6}$ alkyl, wherein said alkyl is unsubstituted or substituted with one or more halogen,
(m) —N $R^e R^{e'}$,
(n) —$NR^e$—C(=O)—$R^{e'}$,
(o) —P(=O)$R^e$OH,
(p) —P(=O)$R^e NH_2$,
or
$R^3$ and $R^4$ may be linked to form a carbocyclic group having from 3 to 8 ring atoms, optionally having from one to three ring heteroatoms selected from the group consisting of S, N and O,
wherein said carbocyclic group is unsubstituted or substituted with one or more
(a) halogen,
(b) cyano,
(c) —$NO_2$,
(d) —$C_{1-6}$ alkyl, wherein said alkyl is unsubstituted or substituted with one or more halogen,
(e) —$C_{1-6}$ alkoxy,
(f) —C(=O)—(O)— $R^e$
(g) —C(=O)—$NR^e R^{e'}$
(h) —O—C(=O)— $R^e$
(i) —S—$C_{1-6}$ alkyl,
(j) —$S(O)_x R^e$,
(k) —$S(O)_x NR^e R^{e'}$,
(l) —$S(O)_x NR^e C(=O)C_{1-6}$ alkyl, wherein said alkyl is unsubstituted or substituted with one or more halogen,
(m) —N $R^e R^{e'}$,
(n) —$NR^e$—C(=O)—$R^{e'}$,
(o) —P(=O)$R^e$OH,
(p) —P(=O)$R^e NH_2$,
and $R^e$ and $R^{e'}$ are selected from the same group as $R^c$ and $R^{c'}$;

$R^5$ is selected from the group consisting of
(1) hydrogen,
(2) —$C_{1-10}$ alkyl,
(3) —$C_{2-10}$ alkenyl,
(4) —$C_{2-10}$ alkynyl,
(5) —$C_{0-10}$ alkyl-C(=O)—$R^f$,
(6) —$C_{2-10}$ alkenyl-C(=O)—$R^f$,
(7) —$C_{2-10}$ alkynyl-C(=O)—$R^f$,
(8) —$C_{0-10}$ alkyl-C(=O)—$NR^f R^{f'}$,
(9) —$C_{2-10}$ alkenyl-C(=O)—$NR^f R^{f'}$, and
(10) —$C_{2-10}$ alkynyl-C(=O)—$NR^f R^{f'}$,
wherein said alkyl, alkenyl and alkynyl, are unsubstituted or substituted with one or more
(a) halogen,
(b) cyano,
(c) —$NO_2$,
(d) —$C_{1-6}$ alkyl, wherein said alkyl is unsubstituted or substituted with one or more halogen,
(e) $C_{1-6}$ alkoxy,
(f) —C(=O)—(O)— $R^f$
(g) —C(=O)—$NR^f R^{f'}$
(h) —O—C(=O)— $R^f$
(i) —S—$C_{1-6}$ alkyl,
(j) —$S(O)_x R^f$,
(k) —$S(O)_x NR^f R^{f'}$,
(l) —$S(O)_x NR^f C(=O)C_{1-6}$ alkyl, wherein said alkyl is unsubstituted or substituted with one or more halogen,
(m) —$NR^f R^{f'}$,
(n) —$NR^f$—C(=O)—$R^{f'}$,
(o)—P(=O)$R^f$OH,
(p) —P(=O)$R^f NH_2$, and
and $R^f$ and $R^{f'}$ are selected from the same group as $R^c$ and $R^{c'}$;

x is 1 or 2;

provided that formula III is linked at one of $R^2$ and $R^5$ to (2R)-2-propyloctanoic acid; and pharmaceutically acceptable salts thereof.

Additionally, when one of $R^2$ or $R^5$ is (2R)-2-propyloctanoic acid, the other may be linked to a pharmaceutically active compound that modulates one or more of the biochemical events occurring during stroke.

In one embodiment, $R^1$ is phenyl, which is unsubstituted or substituted with one or more halogen (preferably fluoro).

In one embodiment, $R^2$ is —$OR^c$. In this embodiment, $R^c$ is selected from the group consisting of
(1) hydrogen,
(2) —$C_{1-10}$ alkyl, wherein said alkyl is unsubstituted or substituted with one or more
(a) —$NR^b R^{b'}$,
(b) —C(=O)—$OR^b$, and
(c) —C(=O)—O($C_{1-6}$ alkyl-N($CH_3$)$_3$.

In certain embodiments, $R^3$ and $R^4$ are independently selected from the group consisting of
(1) hydrogen, and
(2) —$C_{1-6}$ alkyl. Preferably, $R^3$ and $R^4$ are each hydrogen.

Nitric Oxide Synthase Inhibitors

Another class of compounds which may be useful $Z^1$ or $Z^2$ moieties is nitric oxide synthase (NOS) inhibitors.

There are three known isoforms of NOS—an inducible form (i-NOS) and two constitutive forms referred to as, respectively, neuronal NOS (n-NOS) and endothelial NOS (e-NOS). Each of these enzymes carries out the conversion of arginine to citrulline, while producing nitric oxide (NO) in response to various stimuli. It is believed that excess NO production by NOS contributes to the pathology of diseases of the central nervous system, such as ischemia. See P. E. Chabrier et al., *Cell Mol Life Sci* (1999) 55:1029-1035. For example, inhibition of n-NOS decreases infarct volume after proximal middle cerebral artery occlusion in the rat, see *J. Cerebr. Blood Flow* 25: 924-929 (1994). In addition, selective iNOS inhibitors were shown to significantly reduce focal cerebral ischemic lesions in rats. See Parmentier et al., *Brit. J Pharmacol* 1999; 127:546-552.

One strategy of improving outcome after stroke is to reduce NO synthesis, to limit the deleterious neurotoxic and pro-inflammatory effects of high concentrations of NO in stroke. Thus, inhibitors of nitric oxide synthase are useful in the treatment of stroke. Suitable nitric oxide synthase inhibitors include non-selective inhibitors, n-NOS inhibitors and i-NOS inhibitors. I-NOS inhibitors are preferred.

An exemplary i-NOS inhibitor for use in the invention is N-(3-(aminomethyl)benzyl)acetamidine (1400W94), which has the structure below:

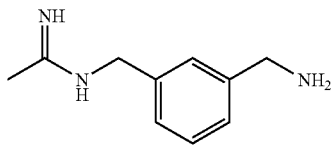

Rho Kinase Inhibitors

Another class of compounds which may be useful as $Z^1$ or $Z^2$ moieties is Rho kinase inhibitors.

Rho kinase inhibitors are compounds that inhibit the activity of family of proteins known as RhoA through E and RhoG (referred to collectively as Rho). The Rho family of proteins plays a critical part in the control of key cellular functions including cell movement, axonal guidance, cytokinesis, and changes in cell morphology, shape and polarity.

Inhibition of Rho kinase activity in animal models has demonstrated a number of potential pharmacologic uses for Rho kinase inhibitors for the treatment of human diseases, including cerebral ischemia. See, e.g., Hitomi, et al. *Life Sci* 2000, 67:1929-1939.

A preferred Rho kinase inhibitor is fasudil, which has the structure

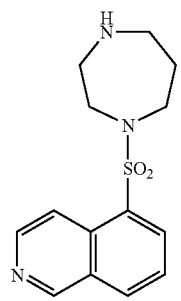

Angiotensin II Type-1 Receptor Antagonists

Another class of compounds which may be useful as $Z^1$ or $Z^2$ moieties is angiotension II (ATII) receptor blockers, which are known to be useful in treating hypertension. ATII stimulates aldosterone release, which contributes to vasoconstriction. ATII may also stimulate the proliferation of cardiovascular tissue, leading to atherosclerosis. See, *Expert Opinion Pharmacother* 2001; 2(11):1795-1804. Hypertension agents act to decrease mortality associated with stroke.

Preferred angiotensin II type-1 receptor antagonists include candesartan (marketed as ATACAND™), losartan (marketed as COZAAR™), irbesartan (marketed as AVAPRO™), eprosartan (marketed as TEVETEN™), telmisartan (marketed as MICARDIS™) and valsartan (marketed as DIOVAN™).

Glycogen Synthase Kinase 3 (GSK3) Inhibitors

Another class of compounds which may be useful as $Z^1$ or $Z^2$ moieties is glycogen synthase kinase 3 (GSK3) inhibitors.

GSK3 is a serine/threonine protein kinase, which is highly expressed in the central and peripheral nervous system. GSK3 is known to phosphorylate several substrates, including tau, B-catenin, glycogen synthase, pyruvate dehydrogenase and elongation initiation factor 2b (eIF2b). Insulin and growth factors activate protein kinase B, which phosphorylates GSK3.

Recent studies indicate that GSK3 activity is increased in cellular and animal models of neurodegeneration such as cerebral ischemia, or after growth factor deprivation. See Bhat et. al., *PNAS* 97:11074-11079 (2000)). Reducing neuronal apoptosis is an important therapeutic goal in stroke, and thus the role of GSK3 as a pro-atopic factor in neuronal cells makes the GSK3a therapeutic target for drugs to treat stroke. See Frame et al, *Biochem J* 2001;359; 1-16. Thus, GSK3 inhibitors could be useful in the treatment of neurodegenerative diseases such as stroke.

p38 MAP Kinase Inhibitors

Another class of compounds which may be useful as $Z^1$ or $Z^2$ moieties is p38 MAP kinase inhibitors.

The p38 mitogen activated protein kinase pathway has a variety of cellular processes. Animal studies have shown that p38 MAP kinase inhibitors are effective in the treatment of several disease models, including myocardial injury. It is believed that p38 MAP kinase inhibitors may be useful in treating stroke. See Lee et al, *Immunopharmacol* 47:185-201 (2000). A preferred p38 MAP kinase inhibitor is SKB 239063, which has the structure:

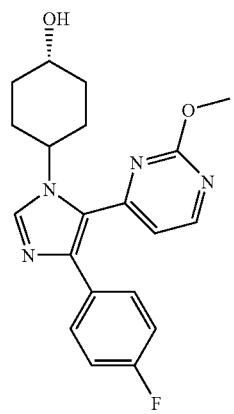

Thromboxane A2-Synthetase Inhibitors

Another class of compounds which may be useful as $Z^1$ or $Z^2$ moieties is thromboxane A2-synthetase (TXA-2) inhibitors.

TXA2 is derived from platelets and monocytes, and acts as a platelet activator. TXA2 also induces vasoconstriction, promotes mitogenesis, and stimulates smooth muscle cell proliferation. An overproduction of TXA2 has been detected in a series of diseases, and TXA2 is believed to contribute to the disease states by stimulation of platelet aggregation and smooth muscle contraction. Increased TXA2 biosynthesis is frequently accompanied by a stimulation of prostacyclin formation, which is one of the most potent inhibitors of platelet aggregation and smooth muscle contraction. Antiplatelet drugs, such as TXA2 synthetase inhibitors, are known to be useful in reducing the risk of stroke. See Tendera et al., *Thrombosis Res* 2003; 110(5-6): 355-359.

Suitable TXA2 synthetase inhibitors for use in the invention include isbogrel, which has the structure:

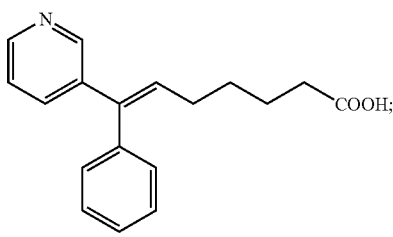

ozagrel, which has the structure:

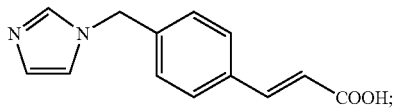

ridogrel, which has the structure:

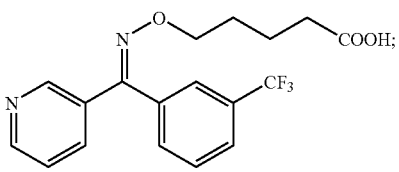

and dazoxiben, which has the structure:

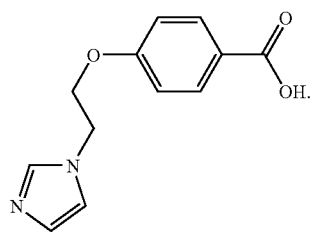

Statins

Another class of compounds which may be useful as $Z^1$ or $Z^2$ moieties is 3-hydroxyl-3-methylglutaryl coenzyme A (HMG-CoA) reductase inhibitors.

HMG-CoA reductase inhibitors, known as statins, competitively inhibit HMG-CoA reductase, which is a regulated reaction in the synthesis of cholesterol. Statins work by upregulating LDL receptor activity, and reducing the entry of LDL into circulation. Statins also have non-lipid lowering effects. For example, statins may upgrade eNOS, inhibit iNOS, attenuate the inflammatory cytokine responses that accompany cerebral ischemia, and relieve ischemic oxidative stress of the brain. See P. Gorelick, *Stroke* 2002, 862-875.

Exemplary statins useful for this invention include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273,995); nisvastatin, also referred to as NK-104 (see PCT international publication number WO 97/23200); and rosuvastatin (see U.S. Pat. No. 5,260,440).

A preferred statin is simvastatin, which has the structure:

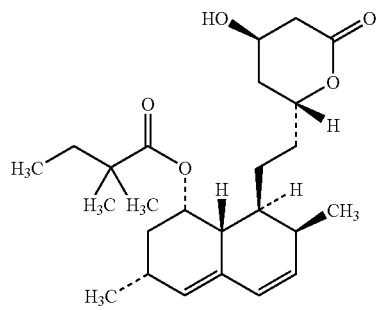

Neuroprotective Agents

Another class of compounds which may be useful as $Z^1$ or $Z^2$ moieties is neuroprotective agents, which are a broad class of agents, which act to prevent brain tissue from injury. Examples of neuroprotective agents include free radical scavengers, calcium channel blockers, excitatory amino acid antagonists, growth factors, and antioxidants.

One class of neuroprotectives are antioxidants. Diets rich in antioxidants have been shown to lower the risk of cardiovascular disease. Antioxidants may help prevent oxidation of LDL-C, thereby inhibiting endothelial damage. Thus, antioxidants may be useful in the treatment of stroke. See P. Gorelick, *Stroke* 2002, 862-875.

A preferred antioxidant for use in the invention is edaravone, which has the structure:

Edaravone, a free radical scavenger, has been shown to inhibit lipid peroxidation and vascular endothelial cell damage in vitro. In rat stroke models, edaravone has been shown to inhibit the development of cerebral edema, cerebral infarction, neurological symptoms and delayed neuronal death. See Kogure et al, *Life Sciences,* 2002; 72(4-5), 575-581.

Other antioxidants which may potentially be used in the invention include Vitamin C, Vitamin E, TROLOX™ (6-hydroxy-2,7,8-tetramethylchroman-2-carboxylic acid):

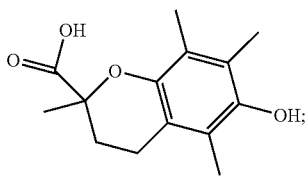

citicoline

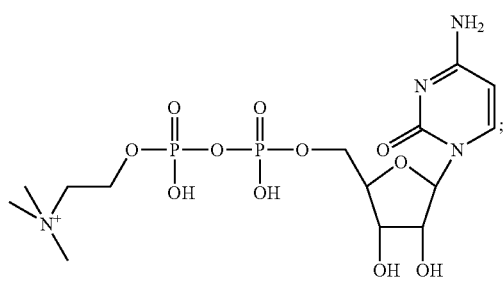

minocycline

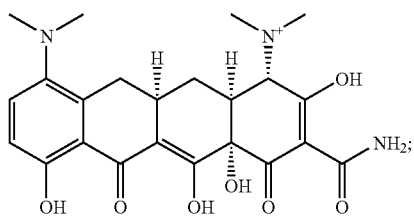

glutathione peroxidase (GPx) mimic BXT-51072, which has the structure:

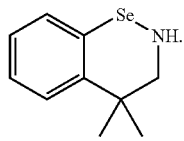

Another class of neuroprotective agents are NMDA receptor antagonists. The N-methyl-D-aspartate (NMDA) receptor is a post synaptic receptor, which has been implicated in neurodegenerative disorders. The NMDA receptor is stimulated by glutamate, and evidence indicates that excessive glutaminergic transmission, or excitotoxicity, underlies neurodegeneration. Thus, NMDA receptor antagonists are potentially effective in treating neurodegeneration, and are known neuroprotective agents. See Bhardwaj et al., *Indian J. Pharmacol.*, 2003, 35:326-327. It has been postulated that NMDA receptor antagonists may be effective in treating acute ischemia. See Parsons et al., *Neuropharmacol.* 1999; 38(6): 735-767. One preferred NMDA receptor antagonist for use in the invention is memantine, which has the structure:

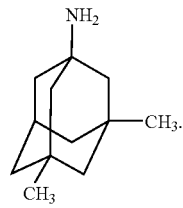

Other preferred NMDA antagonists are dexanabinol, which has the structure:

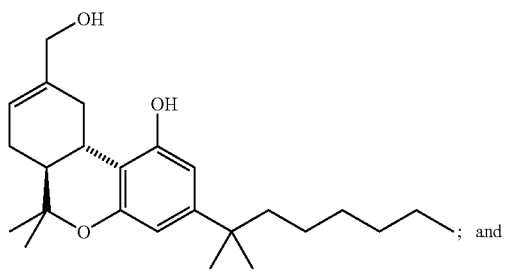

; and traxoprodil, which has the structure:

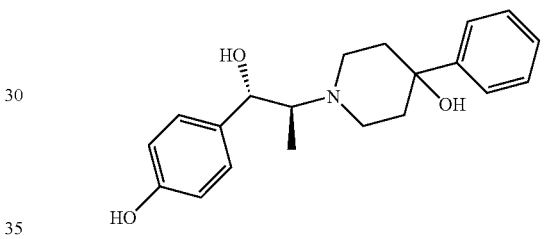

NMDA receptors are heteromeric assemblies of subunits, of which two major subunit families designated NR1 and NR2 have been cloned. The NR2 subunit family is in turn divided into four individual subunit types: NR2A, NR2B, NR2C, and NR2D. T. Ishii, et al., *J. Biol. Chem.*, 268:2836-2843 (1993), and D. J. Laurie et al., *Mol. Brain. Res.*, 51:23-32 (1997) describe how the various resulting combinations produce a variety of NMDA receptors differing in physiological and pharmacological properties such as ion gating properties, magnesium sensitivity, pharmacological profile, as well as in anatomical distribution. The NR2B subunit has been identified as a therapeutic target for various CNS diseases, including stroke. See Chazot, *Curr Med Chem* 2004, 11(3):389-396.

A preferred NR2B antagonist is traxoprodil, which has the structure:

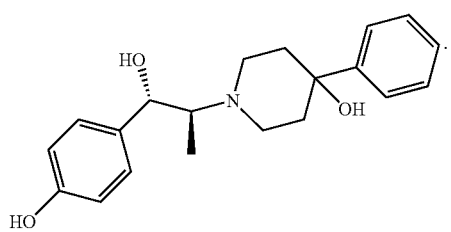

Another class of neuroprotectants useful in the invention is sodium or calcium channel blockers.

Voltage-gated ion channels, such as the sodium and calcium channel, allow electrically excitable cells to generate and propagate action potentials, and thus are crucial for nerve and muscle function. Sodium channels mediate the rapid depolarization, which constitutes the rising phase of the action potential and in turn activates voltage-gated calcium and potassium channels.

Sodium channels are the target of a diverse array of pharmacological agents, including neurotoxins, antiarrhythmics, anticonvulsants and local anesthetics. Evidence from animal models suggest that sodium channel blockers may also be useful for neuroprotection under ischaemic conditions caused by stroke or neural trauma. See Lysko et al, *Stroke* 1994; 25:2476-2482; Aoki et al., *JPET* 2001, 29(6): 306-311.

An exemplary sodium channel blocker is crobenetine, which has the structure:

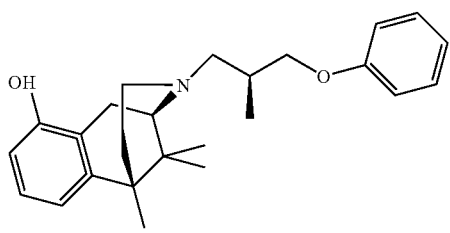

Another class of neuroprotectants are 5-HT1A agonists. The 5-HT1A receptor is highly expressed in areas of the brain, including the hippocampus and cerebral cortex, which are subject to neuronal damage from ischemic stroke. 5-HT1A agonists have been demonstrated to have a neuroprotective effect in rats, and may be effective in the treatment of stroke. See Semkova et al, *Eur J Pharmacol* 1998:359(2-3):251-260.

Exemplary 5-HT1A agonists are repinotan, which has the structure:

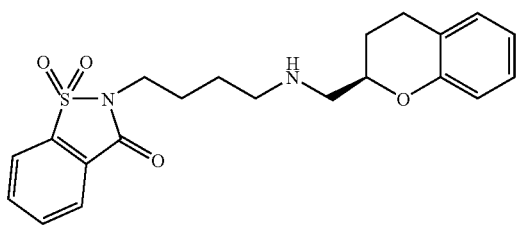

and SUN-N4057, which has the structure:

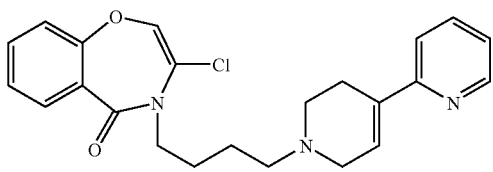

Beta Andrenergic Blockers

Another class of compounds which may be useful as $Z^1$ or $Z^2$ moieties is beta andrenergic blockers.

Beta-andrenergic antagonists (also known as beta blockers) are a class of drugs which are commonly used in treating hypertension, cardiac arrhythmia, and angina pectoris. The beta blockers act by blocking the beta-adrenoceptor, which is an adrenergic receptor which modulates the interaction of norepinephrine and epinephrine. Exemplary beta-adrenergic antagonists for use in the invention include propranolol, nadolol, timolol, pindolol, labetalol, metoprolol, atenolol, esmolol and acebutolol. A preferred beta-adrenergic antagonist is atelol, which has the structure:

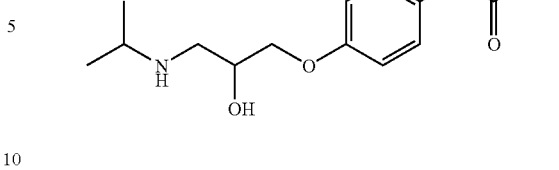

Platelet Fibrinogen Receptor (GPIIb/IIIa) Antagonists

Another class of compounds which may be useful as $Z^1$ or $Z^2$ moieties is glycoprotein IIb/IIIa inhibitors.

Glycoprotein IIb/IIIa (GPIIb/IIIa) is a dimeric receptor which modulates aggregation of blood. The GPIIb/IIIa receptor acts as a receptor for fibrinogen, which fixes platelets and reduces platelet aggregation. Compounds which inhibit the role of the GPIIb/IIIa receptor are antithrombotics, and thus are useful in the treatment of stroke. Exemplary platelet fibrinogen receptor antagonists for use in the invention include abciximas (marketed as REOPRO™) eptifibatide (marketed as INTEGRILIN™), tirofiban (marketed as AGGRASTAT™) and larifiban. Preferred are tirofiban, which has the structure:

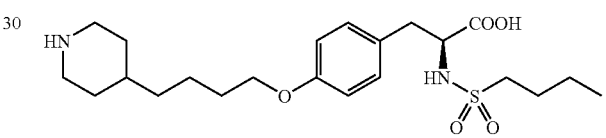

and lamifiban, which has the structure:

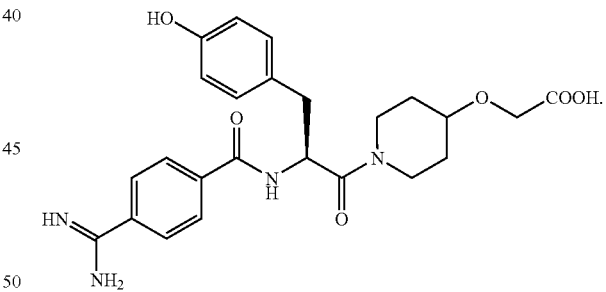

Other neuropharmacologically active compounds which may be effective to treat stroke, and may be useful as $Z^1$ or $Z^2$ moieties are vasodilators, such as cyclandelate, which has the structure:

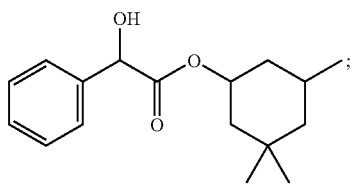

antihypertensive agents, such as enalapril, which has the structure:

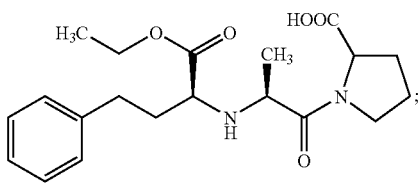

antithrombotics, such as argatroban, which has the structure:

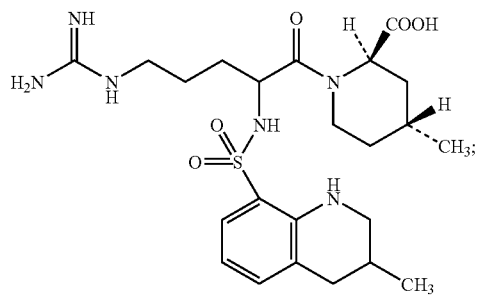

gavestinel, which has the structure:

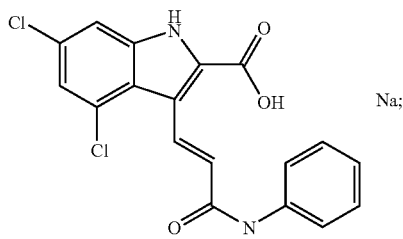

valproic acid (2-propylpentanoic acid), sodium 4-phenyl butyrate, uridine and lithium ion.

Moieties which Impart Favorable Physical Properties

In one embodiment of the compounds of formula (II), the $Z^2$ group is a moiety which imparts a favorable physical property to the prodrug compound of formula (II). In one embodiment, the favorable physical property is increased solubility in an aqueous media. In another embodiment, the favorable physical property is increased stability in an aqueous media.

One moiety which may provide increased solubility in an aqueous media is a quaternary ammonium group, such as a group of compound (IV) below:

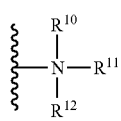

(IV)

wherein $R^{10}$, $R^{11}$ and $R^{12}$ are each alkyl groups (preferably $C_{1-10}$ alkyl), which may be substituted with a hydroxyl. A preferred quaternary ammonium group is choline, which has the structure:

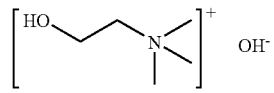

Other preferred groups which may impart solubility to the molecule include phosphate groups, such as groups of formula (V) below:

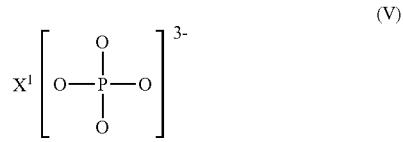

(V)

wherein $X^1$ is $M_3$, $M_2H$ or $MH_2$, wherein M is a metal, such as Na, K, Ca, or a cation, such as $NH4^+$. Phosphate groups useful in the invention include diphosphates.

Other preferred groups which may impart solubility to the molecule include amine salts, such as groups of formula (VI) below:

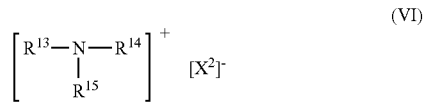

(VI)

wherein $R^{13}$, $R^{14}$ and $R^{15}$ are hydrogen, alkyl, alkenyl, or alkyl-aryl, and $X^2$ is an anion, such as a halogen. Preferred $R^{13}$, $R^{14}$ and $R^{15}$ groups are $C_{1-10}$ alkyl, $C_{2-10}$ alkenyl and $C_{1-4}$ alkyl-$C_{6-10}$ aryl.

Other preferred groups which may impart solubility include sulfonic acids, such as sulfonic acids of the formula (VII) below:

(VII)

wherein $R^{16}$ is alkyl, alkenyl, or alkyl-aryl. Preferred $R^{16}$ groups are $C_{1-10}$ alkyl, $C_{2-10}$ alkenyl and $C_{1-4}$ alkyl-$C_{6-10}$ aryl.

Synthesis of Compounds of the Invention

The compounds of the invention of formula (I) and (II) may be formed by linking (2R)-2-propyloctanoic acid in the carboxylic acid functionality to a $Z^1$ group. In addition, in the compounds of formula (II) the various $Z^1$ and $Z^2$ groups and may be linked according to methods of organic synthesis known to those of ordinary skill in the art. For example, $Z^1$ and $Z^2$ may be linked by standard chemical methods using functionalities present in the particular molecule. Thus, chemists of ordinary skill in the synthesis arts may use standard chemical methods using acid functionalities. For example, a $Z^1$ group having a carboxylic acid moiety may be tethered by removal of the hydrogen to form an anion, which is then reacted with a suitable functionality on a $Z^2$ group to form an ester linkage.

Suitable groups having a carboxylic acid functionality include COX-2 inhibitors, such as the compound of formula (III); ATII type-1 receptor antagonists such as candesartan, eprosartan, telmisartan and valsartan; TXA2 inhibitors such as isbogrel, ozagrel, ridogrel and dazoxiben; statins such as pravastatin, fluvastatin, atorvastatin, rosuvastatin and nisvastatin; antioxidants such as TROLOX™; GPIIb/IIIa antagonists such as tirofiban and lamifiban; and other compounds such as enalapril and valproic acid. Preferred carboxylic acid containing groups include the compound of formula (III), TROLOX™, valproate, sodium 4-phenyl butyrate, candesartan and dazoxiben.

In a second embodiment, suitable $Z^1$ or $Z^2$ groups containing an available hydroxyl functionality may be tethered by removal of the hydrogen from the hydroxyl group to form an oxygen anion. The anion is then linked to a second group through standard chemistry, forming an ether or ester linkage.

For example, as depicted below, a $Z^1$ derivative having a hydroxyl group may be tethered by removal of the hydrogen to form an anion, which is then reacted with a suitable functionality on a $Z^2$ group to form a single compound of the invention:

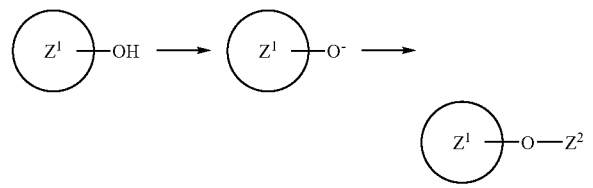

Suitable groups having a hydroxyl functionality include COX-2 inhibitors such as meloxicam; ATII type-1 receptor antagonists such as losartan; p38 MAP kinase inhibitors such as SKB239063; statins such as simvastatin, lovastatin, pravastatin, fluvastatin, atorvastatin, rosuvastatin and nisvastatin; antioxidants such as edaravone, citicoline, minocycline, vitamin C and TROLOX™; beta adrenergic antagonists such as atelol; NMDA receptor antagonists such as dexanabinol; GPIIb/IIIa antagonists such as lamifiban; and other compounds such as cyclandelate and uridine. Preferred hydroxyl containing groups include dexanabinol, minocycline, citicoline, edaravone, SKB 239063, uridine and vitamin C.

In another method of linking $Z^1$ and $Z^2$ groups, chemists of ordinary skill in the synthesis arts may use standard chemical methods to link the compounds at amine functionalities. For example, a $Z^1$ derivative having an amine group may be tethered by removal of the hydrogen to form an anion, which is then reacted with a suitable functionality on a $Z^2$ group to form a single compound having an amino linkage.

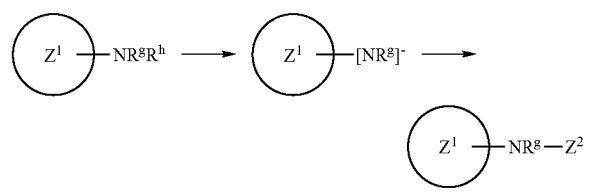

wherein $R^g$ and $R^h$ are hydrogen or a hydrocarbon moiety, or $R^g$ and $R^h$ are linked together with the nitrogen atom to which they are attached to form a cyclic group.

Exemplary groups having an amine functionality include COX-2 inhibitors such as celocoxib; NOS inhibitors such as 1400W94; rho kinase inhibitors such as fasudil; antioxidants such as citicoline and minocycline; beta blockers such as atelol; NMDA receptor antagonists such as memantine; and other compounds such as argatroban. Preferred groups having an amine functionality include 1400W and fasudil.

When the invention is directed to compounds of formula (III), the compounds of the present invention can be prepared according to the following methods:

Method A

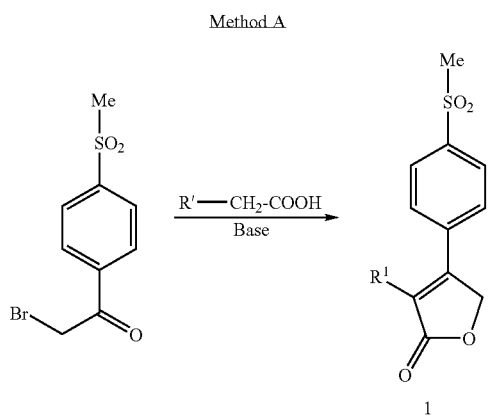

According to Method A, as shown above, an appropriately substituted aryl bromomethyl ketone is reacted with an appropriately substituted aryl acetic acid in a solvent such as acetonitrile in the presence of a base such as triethylamine, and then treated with 1,8-diazabicyclo[5.4.0]undec-7-ene (DBU) to afford the lactone 1.

Method B

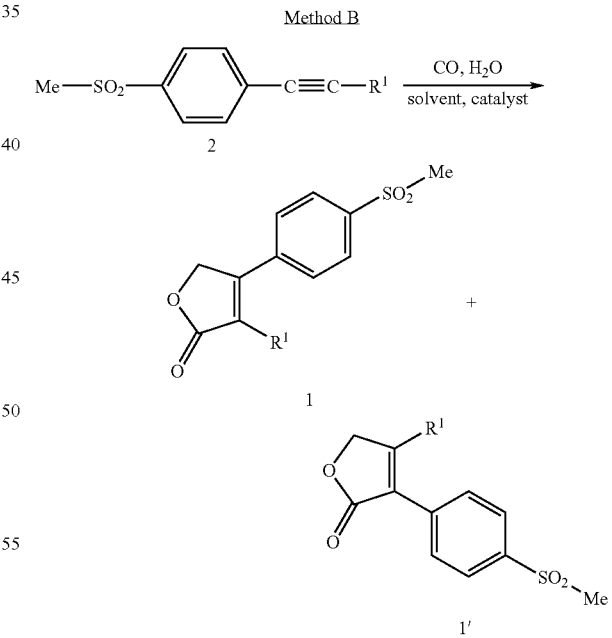

According to Method B, as shown above, a mixture of 1 and its isomer 1' may be obtained by reacting an acetylene 2 with carbon monoxide and water in the presence of a suitable catalyst. The isomers are separable by standard procedures in the art such as chromatography or crystallization. Examples of useful catalysts and conditions are $PdCl_2$ in aqueous HCl and EtOH, heated at 50°-150° C. and 50-150 atmospheres of pressure, or $Rh(CO)_{12}$ (or $Rh_6(CO)_{16}$) in aqueous THF (or acetone, acetonitrile, benzene, toluene, EtOH, MeOH) containing a trialkylamine, at 50°-150° C. and 20-300 atmospheres pressure. See Takahashi et al., *Organometallics* 1991, 10, 2493-2498; and Tsuji et al., *J. Am. Chem. Soc.* 1966, 88, 1289-1292.

Method C

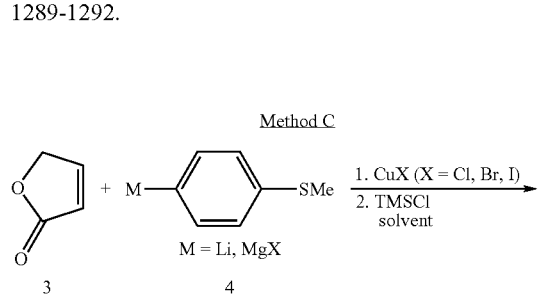

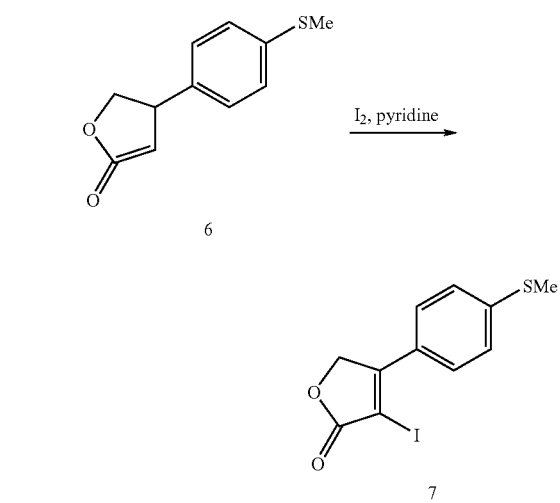

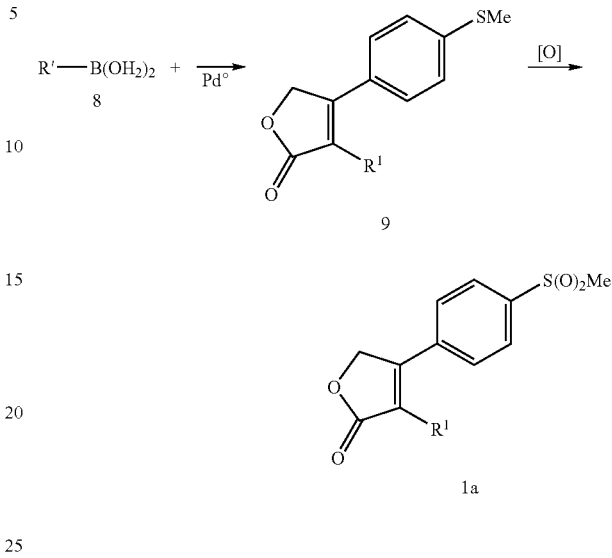

In another method of synthesis, depicted in Method C above, 1,4-addition to 3 of 4-methylthiophenyl organometallic reagents 4 in the presence of copper salts and the trapping of the resultant enolate with trialkyl silyl chloride such as TMSCl or TIPSCl provide the ketene acetal 5. The ketene acetal 5 can then be oxidized to the substituted butenolide 6 by the method of Ito using catalytic amounts of $Pd_2(OAc)_2$ and $Cu(OAc)_2$ and $O_2$ in MeOH or by the method of Magnus using $PhIO/TMSN_3$ and $Bu_4NF$. Introduction of the iodine can be accomplished by treating 6 with $I_2$ in the presence of pyridine to afford 7. Palladium catalyzed Suzuki or Stille coupling of 7 with the appropriate aryl partner such as the boronic acid 8 provides the butenolide 9. The sulfide can be oxidized to a sulfone by various oxidizing agents such as peracetic acid, MPPM, MMPP or $H_2O_2$ to give the desired compound 1a. See Y. Ito et al., *J. Am. Chem. Soc.* 1979, 101, 494, footnote 2, and P. Magnus et al., *Tet. Lett.* 1992, 2933.

Method D

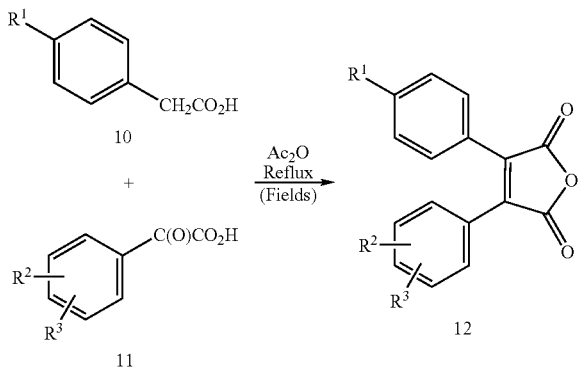

-continued

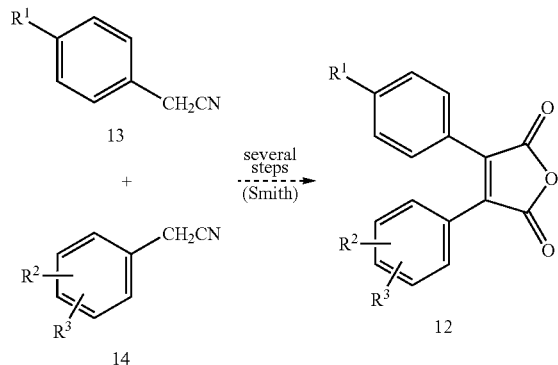

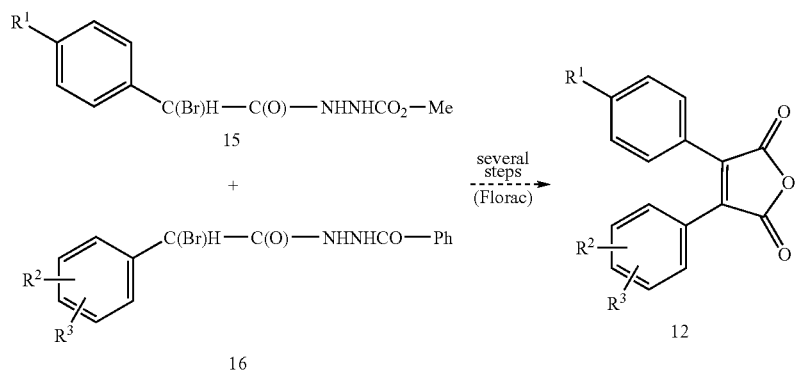

Method D describes methods of synthesis wherein a diaryl furanone is prepared. For example, the 2,3-diphenyl maleic anhydride 12 can be prepared by the method of Fields (*J. Org. Chem.*, 55:5165-70 (1990); U.S. Pat. No. 4,596,867), in which a phenylacetic acid 10 is made to react with an alpha-oxophenylacetic acid 11 (preferably as its potassium salt) in refluxing acetic anhydride.

A multi-step sequence to 12 from phenylacetonitriles such as 13 and 14 is described by Smith, et. al., *J. Org. Chem.*, 55:3351-62 (1990).

Florac et al, in *Tetrahedron*, 46:445-52 (1990) describe another synthesis of 12 in several steps from alpha-bromo phenylaceto hydrazides 15 and 16.

Method E

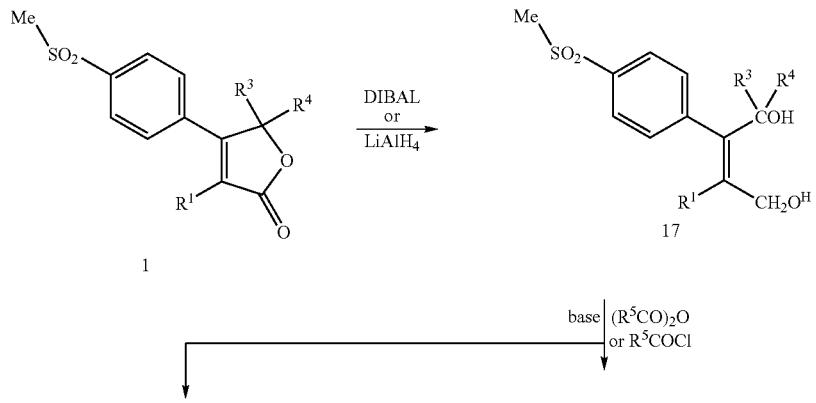

-continued

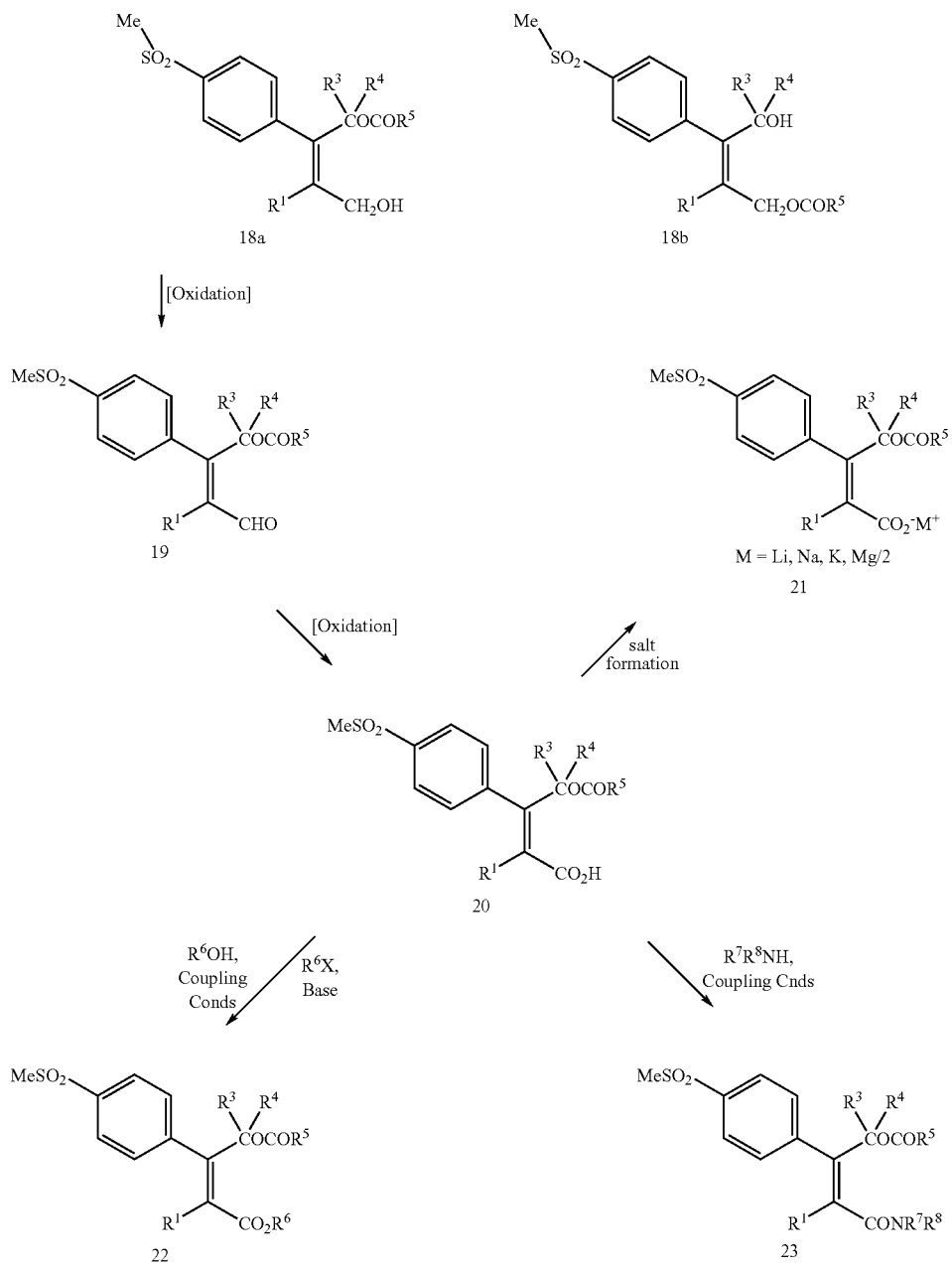

As depicted above in Method E, a lactone 1 may be reduced to the corresponding diol 17 by a suitable reducing agent such as diisobutyl aluminum hydride or lithium aluminum hydride in an appropriate solvent such as toluene, hexane, tetrahydrofuran or ether. The diol 17 is acylated with an anhydride or an acid chloride in the presence of a base such as pyridine, triethylamine or aqueous sodium hydroxide, resulting in the formation of desired isomer 18a and undesired isomer 18b. Isomers 18a and 18b may be separated by chromatography or crystallization. Compound 18a may be oxidized to the aldehyde 19 by a reagent such as manganese dioxide or Dess-Martin periodinane. Aldehyde 19 can then be oxidized to acid 20 with $Cr^{6+}$ reagents, $NaClO_2$ or other suitable oxidants. Base treatment of 20 generates the salt 21.

(2R)-2-propyloctanoic acid may be appended to the free carboxylic acid of 20. If the pharmaceutically active $Z^2$ compound contains a free alcohol ($R^6OH$), it maybe appended to 20 through an ester bond to generate 22 by using suitable coupling conditions such as triphenylphosphine/diisopropylazodicarboxylate or HATU/NMM. If the pharmaceutically active $Z^2$ compound contains a free amine ($R^7R^8NH$), it may be appended to 20 through an amide bond to generate 23 by using suitable coupling conditions such as HATU/NMM.

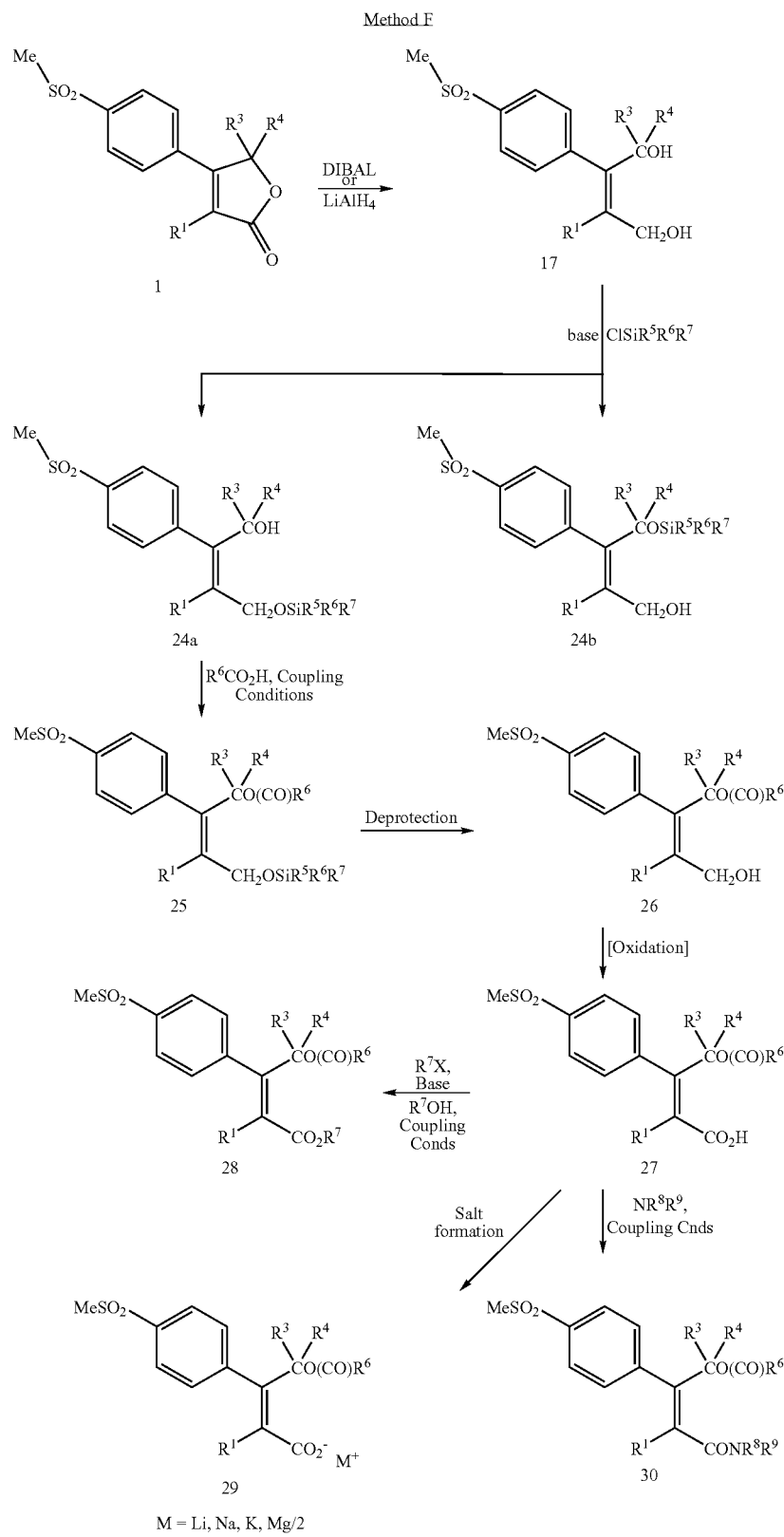
Method F
As depicted above in Method F, a lactone 1 may be reduced to the corresponding diol 17 by a suitable reducing agent such as diisobutyl aluminum hydride or lithium aluminum hydride in an appropriate solvent such as toluene, hexane, tetrahydrofuran or ether. The diol 17 is silylated with a silylchloride in the presence of base resulting in the formation of desired isomer 24a and undesired isomer 24b. Isomers 24a and 24b may be separated by chromatography or crystallization. Alcohol 24a may then be coupled with a carboxylic acid ($R^6CO_2H$), under suitable coupling conditions such as HATU/NMM to give ester 25. Subsequent deprotection of the silyl ether using fluoride gives the free alcohol 26 which may be oxidized to acid 27 with $Cr^{6+}$ reagents, Dess Martin Peridoninane/$NaClO_2$ or other suitable oxidants. Esters 28 can be prepared by reacting 27 with an alkylhalide ($R^7X$) or an alcohol containing amino acid ($R^7OH$), under suitable coupling conditions such as triphenylphosphine/diisopropylazodicarboxylate or HATU/NMM. Alternatively, salt 29 may be prepared by reacting acid 27 with a suitable base. Amides 30 can be prepared by reacting 27 with an amine in the presence of suitable coupling conditions such as HATU/NMM.

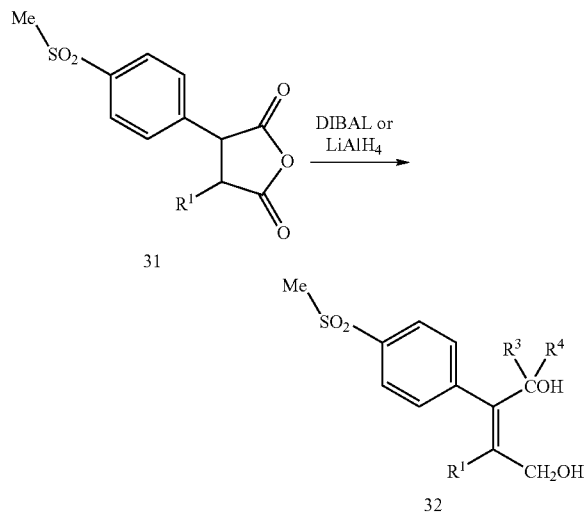

An alternative method of obtaining diol 2 is illustrated in Method G above where a diphenyl maleic anhydride 31 can be reduced to the diol 32 with suitable hydride reducing agents, such as diisobutyl aluminum hydride or lithium aluminum hydride. Solvents such as toluene, tetrahydrofuran or ether, or a mixture thereof, are suitable for the reduction.

The compounds of the invention may have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer of a compound may be obtained by stereoselective synthesis using optically pure starting materials or reagents of known configuration by methods well known in the art.

Pharmaceutical Compositions and Methods of Administration

The compounds of the invention will typically be administered as active ingredients in pharmaceutical compositions, in admixture with suitable pharmaceutical diluents, excipients or carriers (collectively referred to herein as "carrier" materials) suitably selected with respect to the intended form of administration, and consistent with conventional pharmaceutical practices.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The compounds of the invention can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones.

The compounds of the invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the invention may also be delivered by the use of monoclonal antibodies as individual carriers to which the compound molecules are coupled. The compounds may also be coupled with soluble polymers as targetable drug carriers.

The invention is also directed to a therapeutically effective intravenous formulation of the compounds of the invention, which is solution stable and isotonic with human blood. The intravenous formulation preferably can be packaged in plastic or glass, and meets government and compendia (USP in the US) particulate standards, and can be used as effective therapy to treat stroke.

The intravenous formulation may contain a buffer which can maintain the pH of the intravenous formulation within a desirable range. The buffering agent also preferably acts as a complexing agent to maintain metal ions in solution which are leached out of the glass container. Both of these effects, maintaining the lower pH and complexing metal ions, prevents metal ions from precipitating and can maintain the intravenous formulation in an acceptable particulate profile for storage and subsequent use.

Pharmaceutical intravenous formulations of the invention will generally include a therapeutically effective amount of a compound of the invention to treat stroke, in addition to one or more pharmaceutically acceptable excipients. The compositions are advantageously prepared together with liquid inert carriers, such as water. Suitable liquid excipients/carriers are Water for Injection (US Pharmocoepia) and saline solution. The solution should be pyrogen-free, and also should be absent of particulate matter. Limits for the amount of particulate matter (i.e., extraneous, mobile undissolved substances, other than gas bubbles) which may be found in IV fluids are defined in the US Pharmacoepia.

Other suitable excipients and other additives include solvents such as ethanol, glycerol, propylene glycol, and mixtures thereof; stabilizers such as EDTA (ethylene diamine tetraacetic acid), citric acid, and mixtures thereof; antimicrobial preservatives, such as benzyl alcohol, methyl paraben, propyl paraben, and mixtures thereof; buffering agents, such as citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate, and mixtures thereof; tonicity modifiers, such as sodium chloride, mannitol, dextrose, and mixtures thereof; fluid and nutrient replenishers such as synthetic amino acids, dextrose, sodium chloride, sodium lactate, Ringer's solution, and other electrolyte solutions.

The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate. The amount of buffer system used is dependent on the desired pH and the amount of the compound of the invention. The choice of appropriate buffer and pH of a formulation, depending on solubility of the drug to be administered, is readily made by a person having ordinary skill in the art.

By "pharmaceutically acceptable" it is meant the carrier, diluent or excipient must be compatible with the other ingredients of the formulation and not deleterious to the recipient thereof.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

Specific dosages for oral administration of the compounds of the present invention, or pharmaceutically acceptable salts thereof, for administration include 1 mg, 5 mg, 10 mg, 30 mg, 80 mg, 100 mg, 150 mg, 300 mg, 400 mg, 500 mg, 600 mg, 700 mg and 750 mg. Oral pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific oral pharmaceutical compositions useful for treatment may comprise about 1 mg, 5 mg, 10 mg, 30 mg, 80 mg, 100 mg, 150 mg, 300 mg, 400 mg, 500 mg, 600 mg, 700 mg and 750 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The precise dosage by intravenous therapy necessary will vary with the age, size, sex and condition of the subject, the nature and severity of the disorder to be treated, and the like. An effective dose for a compound of the invention in an intravenous liquid formulation is about 1.5 to 3000 μg/kg of body weight, and a useful range is about 10 μg/kg to about 200 μg/kg of body weight. A dosage of 2.5-10 mg per person per day introduced over a 2-10 hour period is a useful intravenous dosage regimen.

The intravenous formulation can be administered by direct intravenous injection, i.v. bolus, or can be administered by infusion by addition to an appropriate infusion solution such as 0.9% sodium chloride injection or other compatible infusion solution.

The compounds of the present invention may be used in combination with one or more other drugs in the treatment of stroke, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefore, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with other drugs or agents that affect receptors or enzymes that either increase the efficacy, safety, convenience, or reduce unwanted side effects or toxicity of the compounds of the present invention.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

The following abbreviations are used throughout the text:
Me: methyl
Et: ethyl
iPr: isopropyl
t-Bu tert butyl
Ac: acetate
THF: tetrahydrofuran
DMAP: 4-dimethylaminopyridine
LDA: lithium diisopropylamide
DMI: 1,3-dimethyl-2-imidazolidinone
DMF: N,N-dimethylformamide
DME: dimethoxyethane
TBAH: tetrabutylammoniumhexafluorophosphate
DCC: dicyclohexylcarbodiimide
TLC: thin layer chromatography
HPLC: high performance liquid chromatography

EXAMPLE 1

Lithium (2R)-2-Propyloctanoate

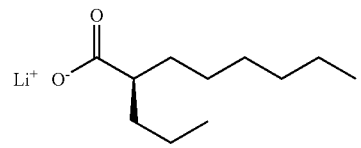

(R)-2-propyloctanoic acid (which is synthesized as taught in *Bull. Chem. Soc. Japan*, 2000, 73:423-428, and in U.S. Pat. No. 6,608,221) (0.10 g, 0.54 mmol) was dissolved in 1 mL EtOH. Aqueous LiOH (1.0N, 0.55 mL, 0.55 mmol) was added and the solution stirred for 30 minutes. The mixture was concentrated under reduced pressure. The residue was dissolved in minimal water and freeze-dried overnight to give the product (Example 1) as a white solid. $^1$H-NMR (D$_2$O, 500 MHz) δ 2.41-2.37 (m, 1H), 1.64-1.41 (m, 14H), 1.08-1.03 (m, 6H). MS (ESI) 185.2 (M−H).

To determine optical purity, the corresponding phenacyl ester (Example 2) was prepared.

EXAMPLE 2

2-Oxo-2-phenylethyl (2R)-2-Propyloctanoate

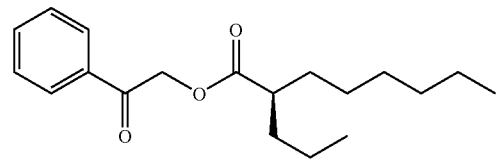

(R)-2-propyloctanoic acid (0.05 g, 0.268 mmol) was dissolved in 5 mL, CH$_2$Cl$_2$. Triethylamine (50 μL, 0.359 mmol) and 2-bromoacetophenone (0.06 g, 0.300) were added, and the reaction was stirred at room temperature for 5 hours. Once no SM was seen by TLC, the reaction mixture was concentrated under reduced pressure to remove all triethylamine.

The residue was purified by silica-gel chromatography (0-10% EtOAc:hexanes) to give the product (Example 2). Ee of >98.5% was determined by HPLC [Chiralcel OJ-RH 4.6× 150 mm; $CH_3CN/H_2O=60/40$; flow rate 1 mL min$^{-1}$; detection, 244 nm; retention time, 10.7 min (S) and 11.9 min (R).]
$^1$H-NMR (CDCl$_3$, 500 MHz) δ 7.91 (d, 2H), 7.61-7.57 (m, 1H), 7.48 (t, 2H), 5.32 (s, 2H), 2.55-2.50 (m, 1H), 1.72-1.68 (m, 2H), 1.52-1.48 (m, 2H), 1.47-1.27 (m, 10H), 0.93 (t, 3H), 0.88 (t, 3H).

EXAMPLE 3

(2Z)-2-(3,4-Difluorophenyl)-3-[4-(methylsulfonyl)phenyl]-4-{[(2R)-2-propyloctanoyl]oxy}but-2-enoic Acid

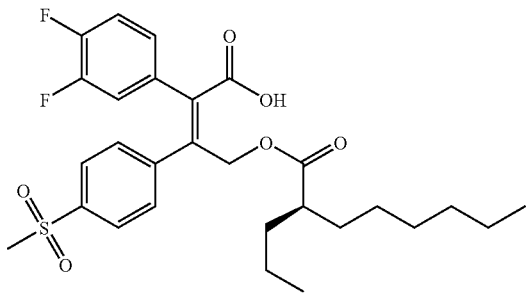

Intermediate 3A (2Z)-4-{[tert-Butyl(dimethyl)silyl]oxy}-3-(3,4-difluorophenyl)-2-[4-(methylsulfonyl)phenyl]but-2-en-1-ol

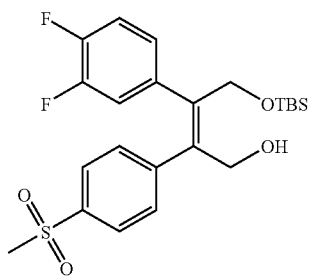

(Z)-2-(4-Methylsulfonyl)Phenyl)-3-(3,4-difluorophenyl)-2-Butene-1,4-diol, which is synthesized as described in U.S. Pat. No. 5,849,943 (Example 10) (5.0 g, 14.12 mmol) was dissolved in 100 mL CH$_2$Cl$_2$. tert-Butyldimethylsilyl chloride (2.11 g, 0.014 mol) and triethylamine (1.96 mL, 0.014 mol) were added, and the reaction was stirred overnight at room temperature. The reaction mixture was adsorbed onto silica gel and purified by silica gel chromatography (25-50% EtOAc:hexanes) to give Intermediate 3A as a white powder.
$^1$H-NMR (CDCl$_3$, 500 MHz) δ 7.74 (d, 2H), 7.27 (d, 2H), 6.96-6.89 (m, 1H), 6.85-6.80 (m, 1H), 6.68-6.64 (m, 1H), 4.60 (s, 2H), 4.55 (d, 2H), 3.08 (s, 3H), 2.65 (t, 1H), 0.89 (s, 9H), 0.03 (s, 6H).

Intermediate 3B (2Z)-4-{[tert-Butyl(dimethyl)silyl]oxy}-3-(3,4-difluorophenyl)-2-[4-(methylsulfonyl)phenyl]but-2-en-1-yl (2R)-2-Propyloctanoate

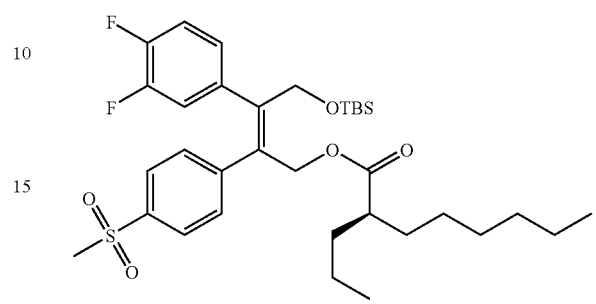

Intermediate 3A (1.0 g, 2.10 mmol) was dissolved in 50 m CH$_2$Cl$_2$. (R)-2-propyloctanoic acid (0.40 g, 2.10 mmol), DCC (0.48 g, 2.33 mmol), and DMAP (0.03 g, 0.21 mmol) were added, and the reaction was stirred at room temperature for 3 hours. After disappearance of starting material as judged by TLC, water was added, and the aqueous layer was extracted three times with CH$_2$Cl$_2$. The combined organic layer was dried over MgSO$_4$, filtered, and concentrated. The residue was purified by silica gel chromatography (0-20% EtOAc:hexanes) to give Intermediate 3B as a colorless oil.
$^1$H-NMR (CDCl$_3$, 500 MHz) δ 7.72 (d, 2H), 7.22 (d, 2H), 6.93-6.83 (m, 2H), 6.68-6.64 (m, 1H), 5.10 (d, 2H), 4.60 (s, 2H), 2.99 (s, 3H), 2.29-2.24 (m, 1H), 1.46-1.09 (m, 14H), 0.89-0.78 (m, 15H), −0.01 (s, 6H).

Intermediate 3C (2Z)-3-(3,4-Difluorophenyl)-4-hydroxy-2-[4-(methylsulfonyl)phenyl]but-2-en-1-yl (2R)-2-Propyloctanoate

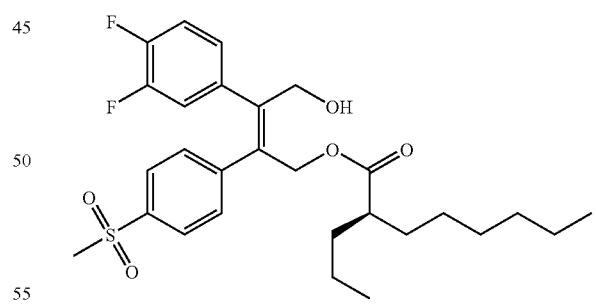

Intermediate 3B (0.80 g, 1.25 mmol) was dissolved in 15 mL THF and cooled to 0° C. HF.pyridine (1.0 mL, 6.25 mmol) was added dropwise, and the reaction mixture was stirred at room temperature for 2 hours. After disappearance of starting material as judged by TLC, the solution was made basic by the dropwise addition of aqueous NaHCO$_3$ (sat.). The aqueous layer was extracted three times with EtOAc. The combined organic layer was dried over MgSO$_4$, filtered, and concentrated. The residue was purified by silica gel chromatography (0-50% EtOAc:hexanes) to give Intermediate 3C as a colorless oil. ¹H-NMR (CDCl₃, 500 MHz) δ 7.74 (d, 2H), 7.22 (d, 2H), 6.99-6.88 (m, 2H), 6.78-6.74 (m, 1H), 5.20 (s, 2H), 4.62 (d, 2H), 3.07 (t, 1H), 3.00 (s, 3H), 2.26-2.22 (m, 1H), 1.44-1.10 (m, 14H), 0.86 (t, 3H), 0.79 (t, 3H).

Example 3

(2Z)-2-(3,4-Difluorophenyl)-3-[4-(methylsulfonyl) phenyl]-4-{[(2R)-2-propyloctanoyl]oxy}but-2-enoic Acid Intermediate 3C (0.65 g, 1.24 mmol) was dissolved in 30 mL CH₂Cl₂. Dess-Martin periodinane (0.66 g, 1.55 nmol) was added, and the reaction mixture was stirred at room temperature for 1 hour. Water (1 mL) was added, and the mixture was stirred for an additional 30 minutes at room temperature. The suspension was filtered through a small pad of silica gel and eluted with EtOAc. The filtrate was concentrated to give the crude aldehyde. The residue was dissolved in 20 mL of THF: tBuOH (1:1). 2-methyl-2-butene (5.0 mL of a 2M solution, 10.0 mmol) was added, followed by a solution of NaClO₂ (0.59 g, 6.53 mmol) and NaH₂PO₄ (1.08 g, 9.01 mmol) in water (10 mL). The reaction was stirred for 1 hour until no aldehyde was seen by TLC. EtOAc and H₂O were added, and the aqueous layer was extracted three times with EtOAc. The organic layers were dried over MgSO₄, filtered, and concentrated. The residue was purified by silica gel chromatography (10-75% EtOAc:hexanes) to give the product (Example 3) as a viscous oil. ¹H-NMR (CDCl₃, 500 MHz) δ 7.78 (d, 2H), 7.27 (d, 2H), 6.97-6.91 (m, 2H), 6.78-6.75 (m, 1H), 5.37-5.28 (m, 2H), 3.00 (s, 3H), 2.21-2.17 (m, 1H), 1.39-1.00 (m, 14H), 0.85 (t, 3H), 0.75 (t, 3H). MS (ESI) 535.0 (M−H).

Example 4

2-[((2Z)-2-(3,4-Difluorophenyl)-3-[4-(methylsulfonyl)phenyl]-4-{[(2R)-2-propyloctanoyl]oxy}but-2-enoyl)oxy]-N,N,N-trimethylethanaminium Bromide

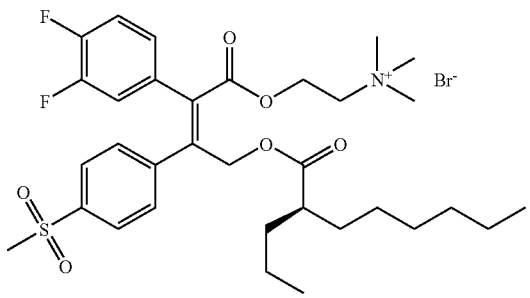

Example 3 (0.25 g, 0.47 mmol) was dissolved in 5 mL DMF. (2-Bromoethyl)trimethyl-ammonium bromide (0.29 g, 1.16 mmol) and K₂CO₃ (0.13 g, 0.96 mmol) were added, and the reaction mixture was stirred at rt for 72 hours. The DMF solution was pipetted away from the K₂CO₃ solid and concentrated under reduced pressure. The residue was purified by silica gel chromatography (1-20% MeOH:CH₂Cl₂) to give Example 7 as an off-white residue. The product was dissolved in minimal H₂O and freeze-dried overnight to give the product (Example 4) as a white solid. ¹H-NMR (MeOD, 500 MHz) δ 7.80 (d, 2H), 7.38 (d, 2H), 7.13-7.07 (m, 2H), 6.92-6.88 (m, 1H), 5.49 (s, 2H), 4.70-4.68 (m, 2H), 3.74-3.71 (m, 2H), 3.06 (s, 9H), 3.05 (s, 3H), 2.17-2.14 (m, 1H), 1.34-1.00 (m, 14H), 0.88 (t, 3H), 0.76 (t, 3H). MS (ESI) 624.15 (M+H).

EXAMPLE 5

5-({1-[(2R)-2-propyloctanoyl]azepan-4-yl}sulfonyl) quinoline

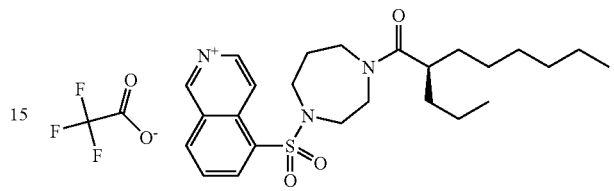

(R)-2-propyloctanoic acid (100 mg, 0.48 mmol) was dissolved in 1 mL DMF. HATU (201 mg, 0.53 mmol) and NMM (64 μL, 0.58 mmol) were added and the solution was stirred for 5 min. Fasudil (154 mg, 0.53 mmol) was added and the solution was stirred for 2 h at rt. The reaction was quenched with TFA (48 μL, 0.63 mmol) and MeOH (1 mL) and purified by preparative HPLC (50% to 100% ACN/water) to give the product (Example 5) as a white solid. ¹H-NMR (500 MHz, CDCl₃) δ 9.81 (s, 1H), 8.94 (d, 1H), 8.70 (d, 1H), 8.54-8.60 (m, 2H), 7.98 (t, 1H), 7.28 (s, 1H), 3.71-3.76 (m, 4H), 3.45-3.48 (m, 4H), 2.56-2.58 (m, 1H), 2.04-2.07 (m, 2H), 1.59-1.65 (m, 2H), 1.43-1.44 (m, 2H), 1.26-1.29 (m, 10H), 0.86-0.91 (m, 6H). MS (ESI) 460 (M+H).

EXAMPLE 6

(2R)—N-{3-[(ethanimidoylamino)methyl]benzyl}-2-ethyloctanamide

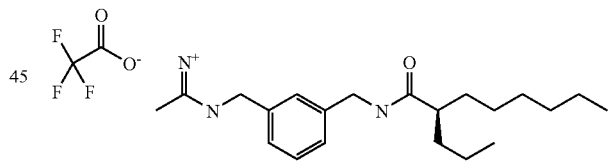

(R)-2-propyloctanoic acid (100 mg, 0.48 mmol) was dissolved in 1 mL DMF. HATU (201 mg, 0.53 mmol) and NMM (192 μL, 1.73 mmol) were added and the solution was stirred for 5 min. 1400-W (94 mg, 0.528 mmol) was added and the solution was stirred for 2 h at rt. The reaction was quenched with TFA (142 μL, 1.87 mmol) TFA and MeOH (1 mL) and purified by preparative HPLC (5% to 100%, ACN/water) to give the product (Example 6) as a white solid. ¹H-NMR (500 MHz, DMSO-d₆) δ 9.80 (s, 1H), 9.22 (s, 1H), 8.76 (s, 1H), 8.37 (t, 1H), 7.34-7.37 (m, 1H), 7.22-7.29 (m, 3H), 4.47 (d, 2H), 4.42 (d, 2H), 2.18-2.24 (m, 4H), 1.46-1.50 (m, 2H), 1.20-1.31 (m, 12H), 0.84-0.87 (m, 6H). MS (ESI) 346 (M+H).

Additional examples include the following compound, in which the compound of formula (III) is linked to (R)-2-propyloctanic acid, as follows:

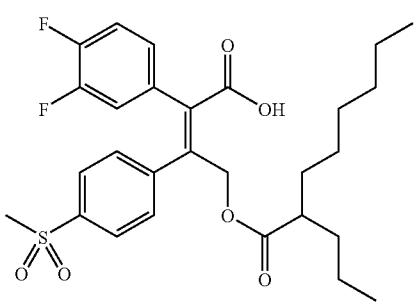

and in which (R)-2-propyloctanoic acid can be linked to dexanabinol, as shown below:

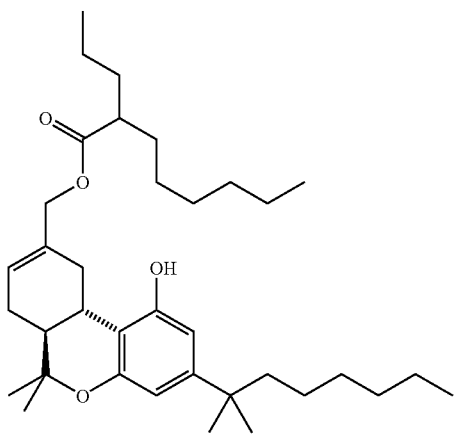

Assays for Determining Biological Activity

The compounds of the invention may be tested using the following assays to determine their biological activity.

Representative Rat Paw Edema Assay

Protocol: Male Sprague-Dawley rats (150-200 g) are fasted overnight and are given p.o., either vehicle (1% methocell) or a test compound in the morning. One hr later, a line is drawn using a permanent marker at the level above the ankle in one hind paw to define the area of the paw to be monitored. The paw volume ($V_{Oh}$) is measured using a plethysmometer (Ugo-Basile, Italy) based on the principle of water displacement. The animals are then injected subplantarly with 50 μl of a 1% carrageenan solution in saline (Sigma Chem) into the paw using an insulin syringe with a 25-gauge needle (i.e., 500 μg carrageenan per paw). Three hr later, the paw volume ($V_{3h}$) is measured and the increases in paw volume ($V_{3h}$-$V_{Oh}$) are calculated. Paw edema data are compared with the vehicle-control group and percent inhibition calculated taking the values in the control group as 100%. All treatment groups are coded to eliminate observer bias.

Rat Aortic Smooth Muscle Flings in Male Sprague-Dawley Rats

Preparation of rat Aortic Smooth Muscle Rings Male Sprague-Dawley rats (Charles River Laboratories, Wilmington, Mass.) are euthanized by interoperation injection of a high dose 5 of sodium pentobarbitone (80-100 mg/kg). The thoracic aorta is rapidly excised and immediately placed in a Petri dish containing warm (37° C.) oxygenated (95% $O_2$ and 5% $CO_2$), Kreb's buffer (composition per millimolar: NaCl (119); KCl (4.69); $CaCl_2.H_2O$ (2.52); $MgSO_4.7H_2O$ (0.57); $NaHCO_3$ (25); $NaH_2PO_4.H_2O$ (1.01) and glucose (11.1)). Under a stereoscopic dissecting microscope, the aorta is cleaned, freed from adhering fat and connective tissues. The tissue is cut into ring segments, each approximately 2-3 mm in length.

For experiments to measure relaxation of the tissue under various conditions, a stainless steel tissue holder and an U-shaped stainless steel wire are inserted into the lumen of the aortic ring. The tissue holder anchors the ring at the bottom of the organ bath whereas the end of the U-shaped steel wire is tied with fine silk thread so that it connects to the FT-202 transducer. The tissue holder and the steel wire along with the aortic ring are then suspended in a 5-ml doublejacketed temperature-controlled glass organ bath (Radnoti Glass Technology, Inc., Monrovia, Calif.) filled with fresh Kreb's buffer. A mixture of 95% $O_2$ and 5% $CO_2$ is bubbled through a porous sintered disc at the bottom of the bath. The rings are given an initial resting tension of 1.5 g and the preparation is allowed to equilibrate at the initial tension for about 90 min. During this equilibration period, the bath fluid is changed every 15 min and replaced with fresh pre-warmed (37° C.) Kreb's buffer. The isometric tension of the aortic muscle at rest and its response to different stimuli are recorded on a Power Macintosh 6100 computer via a MacLab 8/S computer interface (CB Sciences, Inc. Milford, Mass.) after an initial amplification through a low-noise ETH-400 bioamplifier (CB Sciences, Inc. Milford, Mass.). Contractile responsiveness of the tissue strips is established with 10 TM phenylephrine, and the strips are incubated with the drug for 20 min to establish a steady level of contraction. To test the relaxation effects, test compounds are added to the phenylephrine precontracted strips in the tissue bath at cumulative concentrations of 0.1 TM to 0.1 mM. Concentration of test compounds is increased only after relaxation at the previous concentration reaches a 30 plateau level.

Rat Intra-Venous Dosing Experiment

The in-vivo effectiveness of the compounds disclosed in this patent at releasing the component agents which target two or more distinct mechanisms involved in the biochemical cascade of stroke was determined by dosing rats. Briefly, a suitable quantity of the compound (typically 2 to 10 mg/Kg) was dissolved in a suitable vehicle (e.g. water, saline, PEG 400 or mixtures there of) and administered intravenously to rats. Blood was drawn from the rats at appropriate time-points and was analyzed for either the starting compound and/or one or more of the desired component agents.

Results—Dosing of rats with compounds of the invention led to detection of the component agent or agents in rat blood illustrating the release of the components in-vivo.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I)

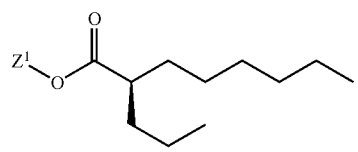

wherein $Z^1$ is a COX-2 inhibitor.

2. The compound of claim 1 which is

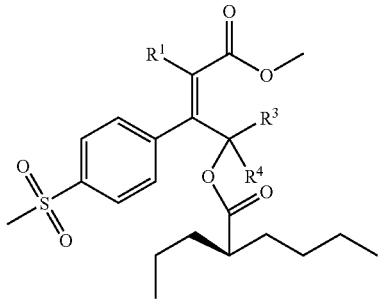

wherein:
R¹ is selected from the group consisting of
(1) -Q-Rᵃ,
(2) a carbocyclic group having from 3 to 8 ring atoms, optionally having from one to three ring heteroatoms selected from the group consisting of S, N and O,
(3) —$C_{6-10}$ aryl, and
(4) heteroaryl,
    wherein said carbocyclic group, aryl and heteroaryl are unsubstituted or substituted with one or more
    (a) halogen,
    (b) cyano,
    (c) $NO_2$,
    (d) —$C_{1-6}$ alkyl, wherein said alkyl is unsubstituted or substituted with one or more halogen,
    (e) —$C_{1-6}$ alkoxy,
    (f) —C(=O)—(O)—$R^b$
    (g) —C(=O)—$NR^b R^{b'}$
    (h) —O—C(=O)—$R^b$
    (i) —S—$C_{1-6}$ alkyl,
    (j) —$S(O)_x R^b$,
    (k) —$S(O)_x NR^b R^{b'}$,
    (l) —$S(O)_x NR^b C(=O)C_{1-6}$ alkyl, wherein said alkyl is unsubstituted or substituted with one or more halogen,
    (m) —$NR^b R^{b'}$,
    (n) —$NR^b$—C(=O)—$R^{b'}$,
    (o) —P(=O)$R^b$OH,
    (p) —P(=O)$R^b NH_2$;
Q is selected from the group consisting of
    (a) —O—,
    (b) —S—,
    (c) —$SO_2$—,
    (d) —$NR^b$;
$R^a$, $R^b$ and $R^{b'}$ are independently selected from the group consisting of:
    (a) hydrogen,
    (b) —$C_{1-10}$ alkyl,
    (c) —$C_{2-10}$ alkenyl,
    (d) —$C_{2-10}$ alkynyl,
    (e) a carbocyclic group having from 3 to 8 ring atoms, optionally having from one to three ring heteroatoms selected from the group consisting of S, N and O,
    (f) —$C_{6-10}$ aryl, and
    (g) heteroaryl,
        wherein said carbocyclic group, alkyl, alkenyl, alkynyl, aryl and heteroaryl are unsubstituted or substituted with one or more
        (i) halogen,
        (ii) cyano,
        (iii) —$NO_2$,
        (iv) —$C_{1-6}$ alkyl, wherein said alkyl is unsubstituted or substituted with one or more halogen,
        (v) —$C_{1-6}$ alkoxy,
        (vi) —C(=O)—(O)—$R^c$
        (vii) —C(=O)—$NR^c R^{c'}$
        (viii) —O—C(=O)—$R^c$
        (ix) —S—$C_{1-6}$ alkyl,
        (x) —$S(O)_x R^c$,
        (xi) —$S(O)_x NR^c R^{c'}$,
        (xii) —$S(O)_x NR^c C(=O)C_{1-6}$ alkyl, wherein said alkyl is unsubstituted or substituted with one or more halogen,
        (xiii) —N $R^c R^{c'}$,
        (xiv) —$NR^c$—C(=O)—$R^{c'}$,
        (xv) —P(=O)$R^c$OH,
        (xvi) —P(=O)$R^c NH_2$,
        and $R^c$ and $R^{c'}$ are independently selected from the group consisting of
        (A) hydrogen,
        (B) —$C_{1-10}$ alkyl,
        (C) —$C_{2-10}$ alkenyl,
        (D) —$C_{2-10}$ alkynyl,
        (E) a carbocyclic group having from 3 to 8 ring atoms, optionally having from one to three ring heteroatoms selected from the group consisting of S, N and O,
        (F) —$C_{0-10}$ alkyl-$C_{6-10}$ aryl, and
        (G) heteroaryl;
R³ and R⁴ are independently selected from the group consisting of
(1) hydrogen,
(2) —$C_{1-10}$ alkyl,
(3) —$C_{2-10}$ alkenyl,
(4) —$C_{2-10}$ alkynyl,
(5) —$C_{6-10}$ aryl, or
(6) heteroaryl,
    wherein said alkyl, alkenyl, alkynyl, aryl and heteroaryl are unsubstituted or substituted with one or more
    (a) halogen,
    (b) cyano,
    (c) $NO_2$,
    (d) $C_{1-6}$ alkyl, wherein said alkyl is unsubstituted or substituted with one or more halogen,
    (e) —$C_{1-6}$ alkoxy,
    (f) —C(=O)—(O)—$R^e$
    (g) —C(=O)—$NR^e R^{e'}$
    (h) —O—C(=O)—$R^e$
    (i) —S—$C_{1-6}$ alkyl,
    (j) —$S(O)_x R^e$,
    (k) —$S(O)_x NR^e R^{e'}$,
    (l) —$S(O)_x NR^e C(=O)C_{1-6}$ alkyl, wherein said alkyl is unsubstituted or substituted with one or more halogen,
    (m) —N $R^e R^{e'}$,
    (n) —$NR^e$—C(=O)—$R^{e'}$,
    (o) —P(=O)$R^e$OH,
    (p) —P(=O)$R^e NH_2$,
or
R³ and R⁴ may be linked to form a carbocyclic group having from 3 to 8 ring atoms, optionally having from one to three ring heteroatoms selected from the group consisting of S, N and O, wherein said carbocyclic group is unsubstituted or substituted with one or more
    (a) halogen,
    (b) cyano,
    (c) —$NO_2$, (d) —$C_{1-6}$ alkyl, wherein said alkyl is unsubstituted or substituted with one or more halogen,
(e) —$C_{1-6}$ alkoxy,
(f) —C(=O)—(O)—$R^e$
(g) —C(=O)—$NR^eR^{e'}$
(h) —O—C(=O)—$R^e$
(i) —S—$C_{1-6}$ alkyl,
(j) —$S(O)_xR^e$,
(k) —$S(O)_xNR^eR^{e'}$,
(l) —$S(O)_xNR^eC(=O)C_{1-6}$ alkyl, wherein said alkyl is unsubstituted or substituted with one or more halogen,
(m) —N $R^eR^{e'}$,
(n) —$NR^e$—C(=O)—$R^{e'}$,
(o) —P(=O)$R^e$OH,
(p) —P(=O)$R^e$NH$_2$,
and $R^e$ and $R^{e'}$ are selected from the same group as $R^c$ and $R^{c'}$;
$R^5$ is selected from the group consisting of
(1) hydrogen,
(2) —$C_{1-10}$ alkyl,
(3) —$C_{2-10}$ alkenyl,
(4) —$C_{2-10}$ alkynyl,
(5) —$C_{0-10}$ alkyl-C(=O)—$R^f$,
(6) —$C_{2-10}$ alkenyl-C(=O)—$R^f$,
(7) —$C_{2-10}$ alkynyl-C(=O)—$R^f$,
(8) —$C_{0-10}$ alkyl-C(=O)—$NR^fR^{f'}$,
(9) —$C_{2-10}$ alkenyl-C(=O)—$NR^fR^{f'}$, and
(10) —$C_{2-10}$ alkenyl-C(=O)—$NR^fR^{f'}$,
wherein said alkyl, alkenyl and alkynyl, are unsubstituted or substituted with one or more
(a) halogen,
(b) cyano,
(c) —NO$_2$,
(d) —$C_{1-6}$ alkyl, wherein said alkyl is unsubstituted or substituted with one or more halogen,
(e) $C_{1-6}$ alkoxy,
(f) —C(=O)—(O)—$R^f$
(g) —C(=O)—$NR^fR^{f'}$
(h) —O—C(=O)—$R^f$
(i) —S—$C_{1-6}$ alkyl,
(j) —$S(O)_xR^f$,
(k) —$S(O)_xNR^fR^{f'}$,
(l) —$S(O)_xNR^fC(=O)C_{1-6}$ alkyl, wherein said alkyl is unsubstituted or substituted with one or more halogen,
(m) —N $R^fR^{f'}$,
(n) —$NR^f$—C(=O)—$R^{f'}$,
(o) —P(=O)$R^f$OH,
(p) —P(=O)$R^f$NH$_2$, and
and $R^f$ and $R^{f'}$ are selected from the same group as $R^c$ and $R^{c'}$;
x is 1 or 2;
and pharmaceutically acceptable salts thereof.

3. A compound of formula (I)

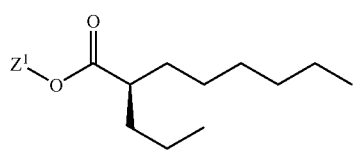

wherein $Z^1$ is a pharmaceutically active compound that modulates one or more of the biochemical events occurring during stroke which is selected from the group consisting of a nitric oxide synthase inhibitor, a Rho kinase inhibitor, an angiotension II type-1 receptor antagonist, a glycogen synthase kinase 3 inhibitor, a sodium or calcium channel blocker, a p38 MAP kinase inhibitor, a thromboxane AX-synthetase inhibitor, a statin, an antioxidant, a beta andrenergic blocker, a NMDA receptor antagonist, a platelet fibrinogen receptor antagonist, a thrombin inhibitor or a vasodilator.

4. A method of treating stroke, comprising administering a compound of claim 1 to a stroke patient.

5. A pharmaceutical composition comprising a compound of claim 1.

6. A compound of formula (II)

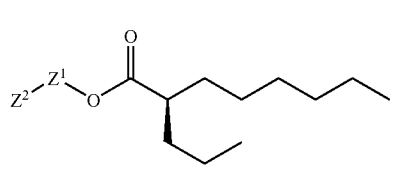

wherein $Z^2$ is covalently bonded to $Z^1$,
and $Z^1$ modulates one or more of the biochemical events occurring in stroke;
$Z^2$ is a moiety which modulates one or more of the biochemical events occurring in stroke or is a moiety which imparts solubility in aqueous media to the compound of formula (I).

7. The compound of claim 6 which is

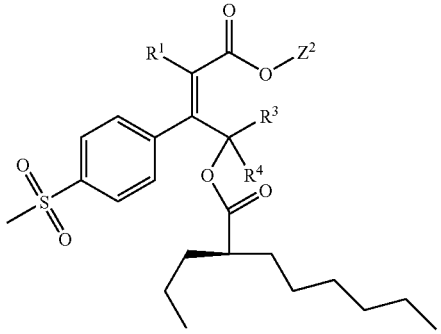

wherein:
$R^1$ is selected from the group consisting of
(1) -Q-$R^a$,
(2) a carbocyclic group having from 3 to 8 ring atoms, optionally having from one to three ring heteroatoms selected from the group consisting of S, N and O,
(3) —$C_{6-10}$ aryl, and
(4) heteroaryl,
wherein said carbocyclic group, aryl and heteroaryl are unsubstituted or substituted with one or more
(a) halogen,
(b) cyano,
(c) NO$_2$,
(d) —$C_{1-6}$ alkyl, wherein said alkyl is unsubstituted or substituted with one or more halogen,
(e) —$C_{1-6}$ alkoxy,
(f) —C(=O)—(O)—$R^b$
(g) —C(=O)—$NR^bR^{b'}$
(h) —O—C(=O)—$R^b$
(i) —S—$C_{1-6}$ alkyl,
(j) —$S(O)_xR^b$, (k) —S(O)$_x$NR$^b$R$^{b'}$,
(l) —S(O)$_x$NR$^b$C(=O)C$_{1-6}$ alkyl, wherein said alkyl is unsubstituted or substituted with one or more halogen,
(m) —NR$^b$R$^{b'}$,
(n) —NR$^b$—C(=O)—R$^{b'}$,
(o) —P(=O)R$^b$OH,
(p) —P(=O)R$^b$NH$_2$;

Q is selected from the group consisting of
(a) —O—,
(b) —S—,
(c) —SO$_2$—,
(d) —NR$^b$;

R$^a$, R$^b$ and R$^{b'}$ are independently selected from the group consisting of:
(a) hydrogen,
(b) —C$_{1-10}$ alkyl,
(c) —C$_{2-10}$ alkenyl,
(d) —C$_{2-10}$ alkynyl,
(e) a carbocyclic group having from 3 to 8 ring atoms, optionally having from one to three ring heteroatoms selected from the group consisting of S, N and O,
(f) —C$_{6-10}$ aryl, and
(g) heteroaryl,
wherein said carbocyclic group, alkyl, alkenyl, alkynyl, aryl and heteroaryl are unsubstituted or substituted with one or more
(i) halogen,
(ii) cyano,
(iii) —NO$_2$,
(iv) —C$_{1-6}$ alkyl, wherein said alkyl is unsubstituted or substituted with one or more halogen,
(v) —C$_{1-6}$ alkoxy,
(vi) —C(=O)—(O)—R$^c$
(vii) —C(=O)—NR$^c$R$^{c'}$
(viii) —O—C(=O)—R$^c$
(ix) —S—C$_{1-6}$ alkyl,
(x) —S(O)$_x$R$^c$,
(xi) —S(O)$_x$NR$^c$R$^{c'}$,
(xii) —S(O)$_x$NR$^c$C(=O)C$_{1-6}$ alkyl, wherein said alkyl is unsubstituted or substituted with one or more halogen,
(xiii) —N R$^c$R$^{c'}$,
(xiv) —NR$^c$—C(=O)—R$^{c'}$,
(xv) —P(=O)R$^c$OH,
(xvi) —P(=O)R$^c$NH$_2$,
and R$^c$ and R$^{c'}$ are independently selected from the group consisting of
(A) hydrogen,
(B) —C$_{1-10}$ alkyl,
(C) —C$_{2-10}$ alkenyl,
(D) —C$_{2-10}$ alkynyl,
(E) a carbocyclic group having from 3 to 8 ring atoms, optionally having from one to three ring heteroatoms selected from the group consisting of S, N and O,
(F) —C$_{0-10}$ alkyl-C$_{6-10}$ aryl, and
(G) heteroaryl;

R$^3$ and R$^4$ are independently selected from the group consisting of
(1) hydrogen,
(2) —C$_{1-10}$ alkyl,
(3) —C$_{2-10}$ alkenyl,
(4) —C$_{2-10}$ alkynyl,
(5) —C$_{6-10}$ aryl, or
(6) heteroaryl,
wherein said alkyl, alkenyl, alkynyl, aryl and heteroaryl are unsubstituted or substituted with one or more
(a) halogen,
(b) cyano,
(c) NO$_2$,
(d) C$_{1-6}$ alkyl, wherein said alkyl is unsubstituted or substituted with one or more halogen,
(e) —C$_{1-6}$ alkoxy,
(f) —C(=O)—(O)— R$^e$
(g) —C(=O)—NR$^e$R$^{e'}$
(h) —O—C(=O)— R$^e$
(i) —S—C$_{1-6}$ alkyl,
(j) —S(O)$_x$R$^e$,
(k) —S(O)$_x$NR$^e$R$^{e'}$,
(l) —S(O)$_x$NR$^e$C(=O)C$_{1-6}$ alkyl, wherein said alkyl is unsubstituted or substituted with one or more halogen,
(m) —N R$^e$R$^{e'}$,
(n) —NR$^e$—C(=O)—R$^{e'}$,
(o) —P(=O)R$^e$OH,
(p) —P(=O)R$^e$NH$_2$,
or R$^3$ and R$^4$ may be linked to form a carbocyclic group having from 3 to 8 ring atoms, optionally having from one to three ring heteroatoms selected from the group consisting of S, N and O,
wherein said carbocyclic group is unsubstituted or substituted with one or more
(a) halogen,
(b) cyano,
(c) —NO$_2$,
(d) —C$_{1-6}$ alkyl, wherein said alkyl is unsubstituted or substituted with one or more halogen,
(e) —C$_{1-6}$ alkoxy,
(f) —C(=O)—(O)— R$^e$
(g) —C(=O)—NR$^e$R$^{e'}$
(h) —O—C(=O)— R$^e$
(i) —S—C$_{1-6}$ alkyl,
(j) —S(O)$_x$R$^e$,
(k) —S(O)$_x$NR$^e$R$^{e'}$,
(l) —S(O)$_x$NR$^e$C(=O)C$_{1-6}$ alkyl, wherein said alkyl is unsubstituted
or substituted with one or more halogen,
(m) —N R$^e$R$^{e'}$,
(n) —NR$^e$—C(=O)—R$^{e'}$,
(o) —P(=O)R$^e$OH,
(p) —P(=O)R$^e$NH$_2$,
and R$^e$ and R$^{e'}$ are selected from the same group as R$^c$ and R$^{c'}$;
x is 1 or 2;
and pharmaceutically acceptable salts thereof.

8. The compound of claim 7 wherein Z$^2$ is selected from the group consisting of a COX-2 inhibitor, a nitric oxide synthase inhibitor, a Rho kinase inhibitor, an angiotension II type-1 receptor antagonist, a glycogen synthase kinase 3 inhibitor, a sodium or calcium channel blocker, a p38 MAP kinase inhibitor, a thromboxane AX-synthetase inhibitor, a statin, an antioxidant, a beta andrenergic blocker, a NMDA receptor antagonist, a platelet fibrinogen receptor antagonist, a thrombin inhibitor or a vasodilator.

9. The compound of claim 7 wherein Z$^2$ is a moiety which imparts solubility in aqueous media to the compound of formula (I).

10. The compound of claim 9 wherein Z$^2$ is a quaternary ammonium salt.

11. A pharmaceutical composition comprising a compound of claim 7.

12. A method of treating stroke, comprising administering a compound of claim 7 to a stroke patient.
13. A compound which is selected from the group consisting of:
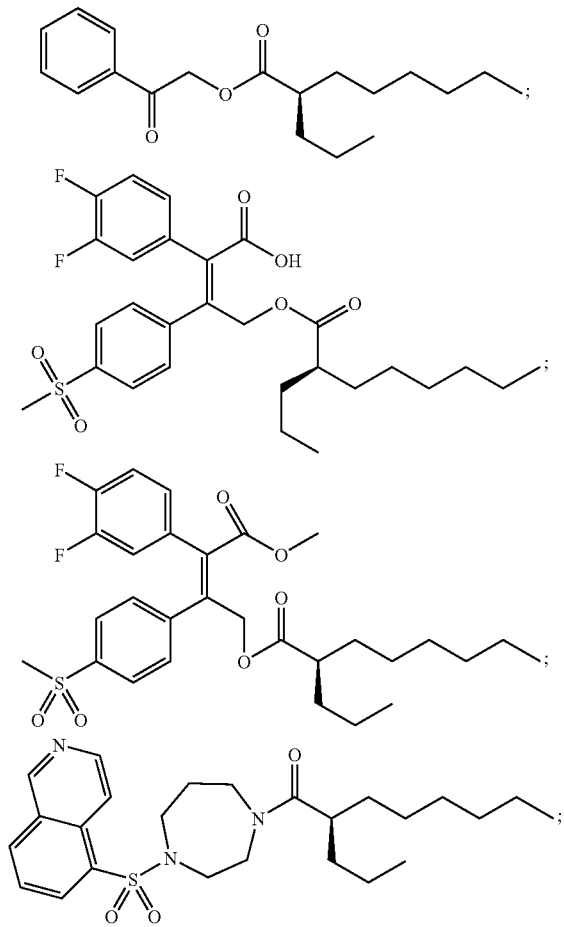
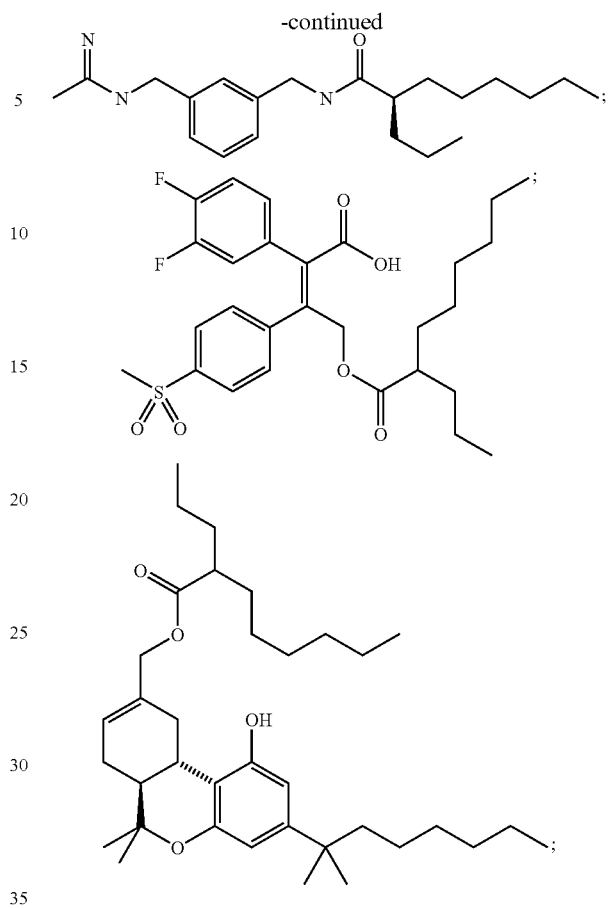
and pharmaceutically acceptable salts thereof.
14. A method of treating stroke, comprising administering a compound of claim 3 to a stroke patient.
15. A pharmaceutical composition comprising a compound of claim 3.
* * * * *